US 11,230,598 B2

(12) United States Patent
Tedder et al.

(10) Patent No.: US 11,230,598 B2
(45) Date of Patent: Jan. 25, 2022

(54) ANTIBODIES AND METHODS FOR DEPLETING REGULATORY BIO CELLS AND USE IN COMBINATION WITH IMMUNE CHECKPOINT INHIBITORS

(71) Applicant: Duke University, Durham, NC (US)

(72) Inventors: Thomas F. Tedder, Durham, NC (US); Yasuhiro Fujisawa, Ibaraki (JP); Jacquelyn Lykken, Durham, NC (US)

(73) Assignee: Duke University, Durham, NC (US)

( * ) Notice: Subject to any disclaimer, the term of this patent is extended or adjusted under 35 U.S.C. 154(b) by 280 days.

(21) Appl. No.: 16/441,917

(22) Filed: Jun. 14, 2019

(65) Prior Publication Data

US 2019/0367607 A1 Dec. 5, 2019

Related U.S. Application Data

(63) Continuation-in-part of application No. PCT/US2017/066815, filed on Dec. 15, 2017.

(60) Provisional application No. 62/434,833, filed on Dec. 15, 2016.

(51) Int. Cl.
| | | |
|---|---|---|
| C07K 16/28 | (2006.01) | |
| A61P 35/00 | (2006.01) | |
| A61K 45/06 | (2006.01) | |

(52) U.S. Cl.
CPC .......... *C07K 16/2803* (2013.01); *A61P 35/00* (2018.01); *A61K 45/06* (2013.01)

(58) Field of Classification Search
CPC ............... C07K 16/2803; C07K 14/42; C07K 2317/24; C07K 2319/55; C07K 16/2818; C07K 16/2887; A61P 35/00; A61K 45/06; A61K 2039/585; A61K 38/164; A61K 38/2013; A61K 2039/505; A61K 2039/507; A61K 39/39; A61K 39/39541
See application file for complete search history.

(56) References Cited

U.S. PATENT DOCUMENTS

| | | | |
|---|---|---|---|
| 4,816,567 A | 3/1989 | Cabilly et al. | |
| 5,298,614 A | 3/1994 | Yano et al. | |
| 5,484,892 A | 1/1996 | Tedder et al. | |
| 6,183,744 B1 | 2/2001 | Goldenberg | |
| 6,187,287 B1 | 2/2001 | Leung et al. | |
| 6,254,868 B1 | 7/2001 | Leung et al. | |
| 6,780,429 B1 | 8/2004 | Matsuyama et al. | |
| 7,438,907 B2 | 10/2008 | Schuurman et al. | |
| 7,534,772 B2 | 5/2009 | Weiner et al. | |
| 7,695,716 B2 | 4/2010 | Drachman et al. | |
| 7,829,086 B2 | 11/2010 | Hilbert | |
| 8,734,792 B2 | 5/2014 | Tedder | |
| 2004/0265315 A1 | 12/2004 | Dingivan et al. | |
| 2006/0120997 A1 | 6/2006 | Lipton | |
| 2008/0253998 A1 | 10/2008 | Andre et al. | |
| 2009/0074711 A1 | 3/2009 | Glennie | |
| 2009/0123467 A1 | 5/2009 | Bedi et al. | |
| 2010/0266680 A1 | 10/2010 | Andre et al. | |
| 2011/0135666 A1 | 6/2011 | Tedder et al. | |
| 2012/0183535 A1 | 7/2012 | Buggy et al. | |
| 2013/0136754 A1 | 5/2013 | Tedder et al. | |
| 2013/0266562 A1 | 10/2013 | Siadak | |
| 2013/0309244 A1 | 11/2013 | Tedder et al. | |
| 2014/0065118 A1 | 3/2014 | Tedder et al. | |
| 2014/0212425 A1 | 7/2014 | Chang | |
| 2016/0159905 A1 | 6/2016 | Abdiche | |
| 2016/0362472 A1 | 12/2016 | Bitter | |

FOREIGN PATENT DOCUMENTS

| | | |
|---|---|---|
| EP | 0404097 | 12/1990 |
| WO | 2002000232 | 1/2002 |
| WO | 2004/053057 | 6/2004 |
| WO | 2004094671 | 11/2004 |
| WO | 2005000901 | 1/2005 |
| WO | 2006121852 | 11/2006 |
| WO | 2004053452 | 8/2007 |
| WO | 2008025848 | 3/2008 |
| WO | 2009/105150 | 8/2009 |
| WO | 2010132659 | 11/2010 |
| WO | 2011147903 | 12/2011 |
| WO | 2012019041 | 2/2012 |
| WO | 2016/164731 | 10/2016 |

OTHER PUBLICATIONS

Brown, et al. J. Immunol. May 1996; 156(9):3285-3291 (Year: 1996).*
Vajdos, et al. J. Mol. Biol. Jul. 5, 2002;320(2); 415-428 (Year: 2002).*
Cheung, et al. FEBS Letters (2014) 588 288-297 (Year: 2014).*
Kunik, et al. PLoS Comput Biol Feb. 2012; 8(2) (Year: 2012).*
Safdari, et al. Biotechnology and Genetic Engineering Reviews, 2013 29:2 176-186 (Year: 2013).*
Liu, R. et al., "A regulatory effect of IL-21 on T follicular helper-like cell and B cell in rheumatoid arthritis," Arthritis Research & Therapy 14(R255):1-12 (2012).
Lund, et al., "Cytokine-producing B lymphocytes—key regulators of immunity," 2008 Curr. Op. Immunol. 20(3):332-338.
Lyons, J.-A. et al., "B cells are critical to induction of experimental allergic encephalomyelitis by protein but not by a short encephalitogenic peptide," 1999 Eur. J. Immunol. 29:3432-3439.
Maini, R.N., et al., How does infliximab work in rheumatoid arthritis, Arthritis Res., 2002, 4 Supp 2:S22-8.

(Continued)

*Primary Examiner* — Julie Wu
*Assistant Examiner* — John L Van Druff
(74) *Attorney, Agent, or Firm* — Quarles & Brady LLP

(57) ABSTRACT

Provided are methods involving combination therapy comprising administering to an individual in need thereof an antibody that preferentially depletes human B10 cells and an immune checkpoint inhibitor. Antibodies for use in the methods are also provided.

20 Claims, 20 Drawing Sheets

Specification includes a Sequence Listing.

(56) References Cited

OTHER PUBLICATIONS

Matsushita, et al., "B-lymphocyte depletion for the treatment of multiple sclerosis: Now things really get interesting," 2009 Expert Rev. Neurotherapeutics 9(3):309-312.
Matsushita, et al., "Inhibitory role of CD19 in the progrssion of experimental autoimmune encephalomyelitis by regulating cytokine response," 2006 Am. J. Path., 168(3):812-821.
Matsushita, T. et al., "Identifying regulatory B cells (B10 cells) that produce IL-10," Methods Mol. Biol. 677, 99-111 (2011).
Matsushita, T. et al., "Regulatory B cells (B10 cells) and regulatory T cells have independent roles in controlling EAE initiation and late-phase immunopathogenesis," J. Immunol. 185, 2240-2252 (2010).
Mauri C., "Regulation of immunity and autoimmunity by B cells," Curr. Opin. Immunol. 22, 761-7657 (2010).
Mauri, C. et al., "The 'short' history of regulatory B cells," 2008, Trends in Immunol. 29: 34-40.
Minard-Colin, V. et al., "Lymphoma depletion during CD20 immunotherapy in mice is mediated by macrophage Fc? RI, Fc?RIII, and Fc?RIV," 2008 Blood 112:1205-1213.
Ozoya, O.O., et al., Hepatitis B reactivation with novel agentsin non-hodgin's lymphoma and prevention strategies, J Clinical and Translation Hepatology, 2016, pp. 143-150, vol. 4.
Parsonnet, J., Bacterial infection as cause of cancer, Environ Health Perspectives, 1995, pp. 263-268, Supp. 8.
Poe, J. C. et al., "Amplified B lymphocyte CD40 signaling drives regulatory B10 cell expansion in mice," PLoS ONE 6, e22464 (2011).
Tuscano, J. M., et al. (1999). CD22 cross-linking generates B-cell antigen receptor-independent signals that activate the JNK/SAPK signaling cascade. Blood, The Journal of the American Society of Hematology, 94(4), 1382-1392.
Uchida, J. et al., "The innate mononuclear phagocyte network depletes B lymphocytes through Fc receptor-dependent mechanisms during anti-CD20 antibody immunotherapy," 2004 J. Exp. Med. 199:1659-1669.
Wehr, C., et al., A new CD21low B cell population in the peripheral blood of patients with SLE, Clin. Immunol., 2004, pp. 161-171, vol. 113.2.
Weitzman, S.A. and Gordon, L.I, et al., Inflammation and cancer: role of phagocyte-generated oxidants in carcinogenesis. Blood, 1990, pp. 655-663, vol. 76.
Xiu, Y. et al., "B lymphocyte depletion by CD20 monoclonal antibody prevents diabetes in nonobese diabetic mice despite isotype-specific differences in Fc?R effector funcitons," 2008, J. Immunol. 180:2863-75.
Yanaba, K. et al., "A regulatory B cell subset with a unique CD1dhiCD5+ phenotype controls T cell-dependent inflammatory responses," Immunity 28, 639-650 (2008).
Yanaba, K. et al., "B cell depletion delays collagen-induced arthritis in mice: Arthritis induction requires synergy between humoral and cell-mediated immunity," 2007, J. Immunol. 179:1369-80.
Yanaba, K. et al., "Regulatory B cells," 2009 Jap. Soc. Clin. Immunol. 32(3):135-141 (Abstract).
Yanaba, K. et al., "The development and function of regulatory B cells expressing IL-10 (B10 cells) requires antigen receptor diversity and TLR signals," J. Immunol. 182, 7459-7472 (2009).
Adachi, O. et al., "Targeted disruption of the MyD88 gene results in loss of IL-1- and IL-18-mediated function," (1998) Immunity 9, 143-150.
Ai, J., et al., The risk of tuberculosis in patients with rheumatoid arthritis treated with tumor necrosis factor—a antagonist: a metaanalysis of both randomized controlled trials and registry/cohort studies, J Rheumatology, 2015, pp. 2229-2237, vol. 4:12.
Anolik, J. H. et al., "New treatments for SLE: Cell-depleting and anti-cytokine therapies," 2005 Best Practice & Research Clinical Rheumatology 19(5):859-878.
Ben-Kasus, T. et al., "Cancer therapeutic antibodies come of age: Targeting minimal residual disease," (2007) Molecular Oncology 1:42-54.
Blair, P.A. et al., "CD19+CD24hiCD38h cells exhibit regulatory capacity in healthy individuals but are functionally impaired in systemic lupus erythematosus patients," 2010 Immunity 32:129-140.
Bouaziz, J.D., et al., "Regulatory B cells as inhibitors of immune responses and inflammation," 2008 Immunol. Rev. 224:201-214.
Brummel, R. et al., "Activation of Marginal Zone B Cells from Lupus Mice with Type A(D) CpG-Oligodeoxynucleotides1," 2005 J. Immunol. 174:2429-34.
Cang, S., et al., Novel CD20 monoclonal antibodies for lymphoma therapy, Journal of Hematology and Oncology, 2012, 5:64.
Cheung, L. S., et al. "Second-generation IL-2 receptor-targeted diphtheria fusion toxin exhibits antitumor activity and synergy with anti-PD-1 in melanoma." Proceedings of the National Academy of Sciences 116.8 (2019): 3100-3105.
Colliou, N. et al., "Long-Term Remissions of Severe Pemphigus After Rituximab Therapy Are Associated with Prolonged Failure of Desmoglein B Cell Response," Science Translational Medicine 5, 175ra30 (2013).
Dilillo, D. J et al., "B10 cells and regulatory B cells balance immune responses during inflammation, autoimmunity, and cancer," Ann. N. Y. Acad. Sci. 1183, 38-57 (2010).
Dzhagalov, I. et al., "The antiapoptotic protein Mcl-1 is essential for the survival of neutrophils but not macrophages," (2007) Blood 109, 1620-1626.
El Zouhairi, M., et al., Molecularly targeted therapy for metastatic colon cancer: proven treatments and promising new agents, Gastrointest Cancer Res., 2011, 15-21,4:1.
Ereno-Orbea, J., et al. "Molecular basis of human CD22 function and therapeutic targeting." Nature communications 8.1 (2017): 1-11.
European Patent Office, Extended European Search Report for application EP17880656.8, dated Jul. 27, 2020. 7 pages.
Federico, et al., Chronic inflammation and oxidative stress in human carcinogenesis, International Journal of Cancer, 2007; pp. 2381-2386, vol. 121.
Fillatreau, S. et al., "B cells regulate autoimmunity by provision of IL-10," Nat. Immunol. 3, 944-950 (2002).
Fillatreau, S., "Novel regulatory functions for Toll-like receptor-activated B cells during intracellular bacterial infection," Immunol. Rev. 240, 52-71 (2011).
Goodnow, C.C. et al.. Altered immunoglobulin expression and functional silencing of self-reactive B lymphocytes in transgenic mice, Nature, 1988, pp. 676-682, vol. 334.
Haas, K. M. et al., "B-1a and B-1b cells exhibit distinct developmental requirements and have unique functional roles in innate and adaptive immunity to *S. pneumoniae*," 2005, Immunity 23:7-18.
Haas, K. M. et al., "Protective and pathogenic roles for B cells during systemic autoimmunity in NZB/W F1 mice," J. Immunol. 184, 4789-4800 (2010).
Haas, K. M. et al., CD22 ligand binding regulates normal and malignant B lymphocyte survival In Vivo, J. Immunol., 2006, pp. 3063-3073, vol. 177.
Hamaguchi, Y. et al., "The peritoneal cavity provides a protective niche for B1 and conventional B lymphocytes during anti-CD20 immunotherapy in mice," (2005) J Immunol 174, 4389-4399.
Harris, D.P. et al., "Reciprocal regulation of polarized cytokine production by effector B and T cells," 2000, Nat. Immunol. 1:475-82.
Hasegawa, M. et al., "B-lymphocyte depletion reduces skin fibrosis and autoimmunity in the tight-skin mouse model for systemic sclerosis," 2006, Am. J. Pathol. 169:954-66.
Hayakawa, I. et al., "B-lymphocyte depletion ameliorates Sjogren's syndrome in Id3 knockout mice," 2007, Immunology 122:73-9.
Horikawa, M. et al., "Regulatory B cell production of IL-10 inhibits lymphoma depletion during CD20 immunotherapy in mice," J. Clin. Invest. 121, 4268-4280 (2011).
Horikawa, M. et al., Regulatory B Cell (B10 Cell) Expansion during Listeria Infection Governs Innate and Cellular Immune Responses in Mice. 2013. J Immunology, pp. 1158-1168, vol. 190.
Huang, J. et al., "Isolation of human monoclonal antibodies from peripheral blood B cells," (2013) Nature Protocols 8:1907 (Abstract).

(56) References Cited

OTHER PUBLICATIONS

Huggins, J. et al., "CpG DNA activation and plasma-cell differentiation of CD27_naive human B cells," Blood 109 (4):1611-1619 (2007).

Inoue, S. et al., "Inhibitory effects of B cells on antitumor immunity," 2006 Cancer Res. 66:7741-7747.

International Preliminary Report on Patentability in International Patent Application No. PCT/US2013/058484 dated Mar. 19, 2015 (8 pages).

International Search Report and Written Opinion in International Patent Application No. PCT/US2009/002560 dated Jul. 20, 2010 (10 pages).

International Search Report and Written Opinion in International Patent Application No. PCT/US2011/046643 dated Mar. 14, 2012 (11 pages).

International Search Report and Written Opinion in International Patent Application No. PCT/US2011/066487 dated May 2, 2012 (10 pages).

International Search Report and Written Opinion in International Patent Application No. PCT/US2013/058484 dated Jan. 10, 2014 (10 pages).

International Search Report and Written Opinion in International Patent Application No. PCT/US2017/066815 dated May 8, 2018 (16 pages).

Iwata, Y. et al., "Characterization of a rare IL-10-competent B cell subset in humans that parallels mouse regulatory B10 cells," Blood 117, 530-541 (2011).

Kandimalla, E.R., et al., Divergent synthetic nucleotide motif recognition pattern: design and development of poten immunomodulatory oligodeoxyribonucleotide agents with distinct cytokine induction profiles, (2003) Nucl. Acid. Res. 31 (9): 2393-2400.

Kansas, G.S. et al., Transmembrane signals generated through MHC class II, CD19, CD20, CD39 and CD40 antigens induce LFA-1-dependent and -independent adhesion in human B cells through a tyrosine kinase-dependent pathway. J Immunol. 1991; 147: 4094-4102.

Kurosaki, T., "Paradox of B cell-targeted therapies," 2008 J. Clin. Inv. 118(10):3260-3263.

Lampropoulou, V. et al., "TLR-activated B cells suppress T cell-mediated autoimmunity," 2008 J. Immunol. 180:4763-4773.

Lebien, T. W., and Tedder, T. F., B-lymphocytes: How they develop and function. Blood, 2008, pp. 1570-1579, vol. 112.

Levesque, M.C. et al., "B cell-directed therapies for autoimmune disease and correlates of disease response and relapse," 2008 J. Allergy Clin. Immunol. 121:13-21.

\* cited by examiner

Days after Treatment Initiation

Figure 22

Amino acid sequence alignment for heavy chain VJ regions of anti-human and anti-mouse CD22 mAbs

```
                                                                        CDR1                                      CDR2
NAME(SEQ ID NO)     1          10         20         30         40         50         60         70
LL2      (1)    QVQLQESGA ELSKPGASVKMSCKASGYTFT-SYWLHWIKQRPGQGLEWIGYINP---RNDYTEYNQNFKDKATLT
HB22-103 (2)    QVQLQQPGT ELVKPGASVKLSCKASGYTFT-SYWMHWVKQRPGQGLEWIGMIHP---NRGTTNYNEKFKSKATLT
HB22-106 (3)    qvqlqqpga eLVKPGASVKLSCKASGYTFT-SYWMHWVKQRPGQGLEWIGMIHP---NSGSTNYSEKFKSKATLT
HB22-115 (4)    QVQLQQPGA ELVKPGASVKLSCKASGYTFT-SYWMHWVKQRPGQGLEWIGMIHP---NSGSTNYSEKFKSKATLT
HB22-107 (5)    DVKLVESGE GLVKPGGSLKLSCAASGFTFS-SYAMSWVRQTPEKRLEWVAYITS---GGDIYYADTVKGRFTIS
RFB4     (6)    EVQLVESGG GLVKPGGSLKLSCAASGFAFS--IYDMSWVRQTPEKRLEWVAYISS---GGGTTYYPDTVKGRFTIS
HB22-13  (7)    EVQLQESGG GLVQPGGSLRLSCATSGFTFI-DYYMNWVRQPPGKALEWLGFIKNKFNGYTEYNTSVKGRFTIS
HB22-23  (8)    EVQLQESGG GLGATWRSMKLSCVASGFTFS-YYWMNWVRQSPEKGLEWIAEIRLKSNNYATHYAESVKGRFTIS
HB22-196 (9)    EVQLQESGP DLVKPGASVKISCKASGYSFI-GYYMHWLKQSHGKSLEWIGRVNP---NTAGLTYNQRFKDKAILT
HB22-5   (10)   EVQLQESGP ELVKPGASMKISCKASGYSFT-DYTMNWVKQSHGKNLEWIGLLHP---FNGGTSYNQKFKGKATLS
M5/44    (11)   EVQLQQSGT VLARPGASVKMSCKASGYTFT-NYWIHWVKQRPGQGLEWIGGINP---GNNYTTYKRNLKGKATLT
HB22-7   (12)   EVQLQESGP GLVAPSQSLSITCTVSGFSLS-DYGVNWVRQIPGKGLEWLGIIWG----DGRTDYNSALKSRLNIS
HB22-33  (13)   EVQLQESGP GLVKPSQSLSLTCSVTGYSITSGYYWNWIRQFPGNKLEWMGYIRY---DGSNNYNPSLKNRISIT CDR3
NAME(SEQ ID NO)    80         90        100
LL2      (1)    ADKSSSTAYMQLSSLTSEDSAVYYCARR-----DITT-EYWGQGTTLTVSS
HB22-103 (2)    VDKSSSTAYMQLSSLTSEDSAVYYCARY------YDYDP-DYWGQGTTLTVSS
HB22-106 (3)    VDKSSSTAYMQLSSLTSEDSAVYYCARY------YDYDP-DYWGQGTTLTVSS
HB22-115 (4)    VDKSSSTAYMQLSSLTSEDSAVYYCARY------YDYDP-DYWGQGTTLTVSS
HB22-107 (5)    RDDARNTLYLQMSSLKSEDTAMYYCTRDQGYYYDGRPTWE-AYWGQGTLVTVSA
RFB4     (6)    RDNAKNTLYLQMSSLKSEDTAMYYCARHSGYGS-SVGVLF-AYWGQGTLVTTSA
HB22-13  (7)    RDNSQSILYLQMNTLRAEDSATYYCARGLGRS------YAM-DYWGQGTSVTVSS
HB22-23  (8)    RDDSKSSVYLQMNNLRAEDTGIYYCTRYDGS------SR-DYWGQGTTLTVSS
HB22-196 (9)    VDKSSNTAYMELRSLTSEDSAVYYCSRVDYDD---YGYWEEDVWGAGTTVTV--
HB22-5   (10)   VDKSSSTAFMELLSLTSEDSAVFECARGTGRN----Y---AM-DYWGQGTTLTVSS
M5/44    (11)   AVTSASTAYMDLSSLTSEDSAVYYCTREGYCGN------YGAWF-AYWGQGTLVTVSS
HB22-7   (12)   KDNSKSQVFLKMNSLKADDTARYYCARAPGN------RAM-EYWGQGTSVTVSS
HB22-33  (13)   RDTSKN-QFLKLNSVTTEDTATYYCARGGIT------VAM-DYWGQGTSVTVSS
```

Figure 22 (Continued)

Amino acid sequence alignment for light chain VJ regions of anti-human and anti-mouse CD22 mAbs

```
                                                                    CDR1                                      CDR2
NAME(SEQ ID NO)        1         10        20                30              40        50              60         70
LL2      (14)   DIQLTQSPSSLAVSAGENVTMSCKSSQSVLYSANHKNYLAWYQQKPGQSPKLLIYWAS TRESGVPDRFTGS
HB22-107 (15)   DIVMIQSPSSLAMSVGQKVTMRCKSSQSLLSSNQKNYLAWYQQKPGQSPKLLVYFAS TRESGVPDRFIGS
HB22-106 (16)   dvvmtqtpltlsvtigqpasisCKKSSQSLLDS-DGKTYLNWLLQRPGQSPKRLIYLVS KLDSGVPDRFSGS
HB22-33  (17)   DVVMTQTPLSLPVSLGDQASISCRSSQSLVHS-NGNTYLHWYLQKPGQSPKLLIYKVS NRFSGVPDRFSGS
M5/44    (18)   DVVVTQTPLSLPVSFGDQVSISCRSSQSLANS-YGNTFLSWYLHKPGQSPQLLIYGIS NRFSGVPDRFTGS
HB22-103 (19)   DIVLTQSPATLSVTPGDSVSLSCRASQSI----SNNLHWFQQKSHESPRLLIKYGY QSISGIPSRFSGS
HB22-115 (20)   DIVLTQSPATLSVTPGDSVTLSCRASQGI----SNNLHWYQQQSHESPRLLIKFTS QSVSGIPSRFSGS
RFB4     (21)   DIQMTQTTSSLSASLGDRVTISCRASQDI----SNYLNWYQQKPDGTVKLLIYYTS ILHSGVPSRFSGS
HB22-196 (22)   NIVMTQSPKSMSMSVGERVTLTCKASENV----VTYVSWYQQKPEQSPKLLIYGAS NRYTGVPDRLTGS
HB22-23  (23)   SIVMTQTPKFLLVSAGDRVTISCKASQSV----SNDVAWYQQKPGQSPKLLIYYAS KRYTGVPDRLTGS
HB22-7   (24)   SIVMTQTPKFLLVSAGDRITLTCKASQSV----TNDVAWYQQKPGQSPKLLIYYAS NRYTGVPDRFTGS
HB22-5   (25)   SIVMTQTPKFLLVSTGDRVTITCKASQTV----TNDLAWYQQKPGQSPKLLIYYAS NRYTGVPDRFTGS
HB22-13  (26)   SIVMTQTPKFLLVSAGDRVSITCKASQSV----TNDVTWYQQKPGQSPKLLIYFAS NRYTGVPDRFTGS CDR3
NAME(SEQ ID NO)     80           90         100
LL2      (14)   GSGTDFTLTISRVQVEDLAIYYCHQ-YLSSWTFGGGTKLEIK      112
HB22-107 (15)   GSGTDFTLTINSVQAEDLADYFCQQHYSTPLTFGAGTKLELK      113
HB22-106 (16)   GSGTDFTLKISRVEAEDLGVYYCWQGTHFPRTFGGGTKLEIK      113
HB22-33  (17)   GSGTDFTLKISRVEAEDLGVYFCSQSTHVPYTFGGGTKLEIK      112
M5/44    (18)   GSGTDFTLKISTIKPEDLGMYYCLQGTHQPYTFGGGTKLEIK      112
HB22-103 (19)   GSGTDFTLSINSVETEDFGMYFCQQSYRWPYTFGGGTKLEIK      107
HB22-115 (20)   GSGTDFTLSVNSVETEDFGMYFCQQSNRWPYTFGGGTKLEIK      107
RFB4     (21)   GSGTDYSLTISNLEQEDFATYFCQQGNTLPWTFGGGTKLEIK      107
HB22-196 (22)   GSATDFTLTISSVQAEDLADYHCGQYSYPYTFGGGTKLEIK       107
HB22-23  (23)   GYGTDFTFTISTVQAEDLAVYFCQQDHSYPWTFGGGTKLEIK      107
HB22-7   (24)   GYGTDFTFTISTVQAEDLAVYFCQQDYRSPWTFGGGTKLEIK      107
HB22-5   (25)   GYGTDFTFTINTVQAEDLAVYFCQQDYSSPLTFGAGTKLELK      107
HB22-13  (26)   GYGTDFTFTISTVQAEDLAVYFCQQDYSSPLTFGAGTKLELK      107
```

ANTIBODIES AND METHODS FOR DEPLETING REGULATORY B10 CELLS AND USE IN COMBINATION WITH IMMUNE CHECKPOINT INHIBITORS

CROSS-REFERENCE TO RELATED APPLICATIONS

This patent application is a continuation-in-part of PCT Application No. PCT/US2017/066815 filed on Dec. 15, 2017 which claims the benefit of priority of U.S. Provisional Patent Application No. 62/434,833, filed Dec. 15, 2016, which is incorporated herein by reference in its entirety.

SEQUENCE LISTING

This application is being filed electronically via EFS-Web and includes an electronically submitted Sequence Listing in .txt format. The .txt file contains a sequence listing entitled "2017-12-15_5667-00417_ST25.txt" created on Dec. 15, 2017 and is 32,337 bytes in size. The Sequence Listing contained in this .txt file is part of the specification and is hereby incorporated by reference herein in its entirety.

FIELD OF THE INVENTION

Provided herein are methods in which an antibody that preferentially depletes regulatory B10 cells and treatments that regulate immune checkpoint pathways are administered to an individual in a combination treatment regimen. The methods can be used to treat any disease or condition that would benefit from such combination therapy. The methods may be used to initiate or activate a pre-existing adaptive immune response, such as an anti-tumor response against cancers such as leukemias, lymphomas, multiple myeloma, and solid nonlymphoid tumors that are also treated using an immune checkpoint inhibitor. Also provided are CD22 specific antibodies for use in the methods and treatments.

BACKGROUND OF THE INVENTION

Regulatory B10 cells ("B10 cells") have the capacity to produce IL-10, and are characterized by their ability to restrain inflammatory and autoimmune immune responses in vivo. One way in which B10 cells can regulate inflammation and autoimmune responses is by their ability to suppress the activation or effector function of lymphocytes and cells of the innate immune system, and their pro-inflammatory cytokine production. Alternatively, various immune checkpoint receptors, such as LAG-3, affect both effector T cells and regulatory T (Treg) cells. Like most mature B cells, human B10 cells express CD19, CD20, CD21, and CD22 on their cell surface. Additionally, as known to those skilled in the art, human blood B10 cells are predominately CD27$^+$, with most being CD24$^{hi}$CD27$^+$, particularly for adults; whereas in children, blood B10 cells tend to express a CD24$^{hi}$CD38$^{hi}$ cell surface phenotype.

Anti-CD22 antibodies have been described, for example in U.S. Pat. Nos. 5,484,892; 6,183,744; 6,187,287; 6,254,868; 7,829,086; 8,734,792 and in Tuscano et al., Blood 94(4):1382-92 (1999). The use of monoclonal antibodies, including anti-CD22 antibodies, in the treatment of lymphoma, leukemia and autoimmune diseases is described. In general these treatments relied on the antibody killing B cells via antibody-dependent cell-mediated cytotoxicity (ADCC) or complement dependent cell-mediated cytotoxicity (CDC) and the use of the antibodies to treat cancer was limited to B cell lymphoma and leukemia.

Immune checkpoint inhibitors are molecules or drugs that block or engage certain proteins (immune checkpoint receptors or their ligands) that are expressed by some types of immune system cells, such as T cells, macrophages, as well as by some cancer cells. Overall, immune checkpoint proteins and their functional pathways help keep immune responses in check; however, they can also inhibit the activation of T cells and suppress the immune system, thereby preventing T cells from responding to or killing cancer cells. When these proteins are blocked, their suppressive effect on the immune system is released, allowing T cells to respond to tumor antigens and become programmed to kill cancer cells. Immune checkpoints can also limit the duration and intensity of T cell responses. As known to those skilled in the art, examples of checkpoint proteins found on T cells or cancer cells include, but are not limited to, PD-1, PD-L1, CTLA-4 (also known as CD152), 4-1BB (also known as CD137), LAG-3, and OX40 (a TNF receptor family member). Some immune checkpoint inhibitors are used to treat cancer. In the clinic, immune checkpoint inhibitors such as anti-PD1 antibody and anti-CTLA-4 antibody have shown induced objective response rates ranging from about 10% to about 35%, with about 22% of patients achieving long term survival benefit, depending on such factors as the immune checkpoint inhibitor used, dose, immune status of the individual treated, stage of disease, and the type of cancer treated. For the treatment of most cancers, and in particular lymphomas and leukemias, there continues to be a need for improved or new therapeutic treatments.

SUMMARY OF THE INVENTION

The methods presented herein are based at least in part on the surprising discovery of synergy in effecting T cell activation (T cells comprising one or more of CD4$^+$ cells and CD8$^+$ cells) as a result of combining an antibody that preferentially depletes regulatory B10 cells with an immune checkpoint inhibitor in combination therapy. In a combination therapy regimen, in administering a combination of a composition comprising an antibody that preferentially depletes regulatory B10 cells and a composition that comprises an immune checkpoint inhibitor, the compositions (in a therapeutically effective amount) may be administered separately, sequentially, intermittently, or together. The compositions of the combination may be formulated as separate compositions or together as a single composition. In one aspect, the methods result in the induction or enhancement of a T cell immune response, or reversing, overcoming or modulating immunosuppression of a pre-existing T cell immune response. Such effects or immunosuppression are also encountered in other diseases (including disorders, and conditions such as in chronic infections (such as hepatitis B and C viruses, lymphocytic choriomeningititis virus, Mycobacterium lepry, and measles virus), and cancers.

In one aspect, provided is a method of immunotherapy which results in T cell activation or re-activation of a pre-existing immune response in an individual in which such pre-existing immune response is inhibited or suppressed, the method comprising administering to the individual a combination therapy regimen comprising a composition comprising an antibody that preferentially depletes regulatory B10 cells and a composition that comprises an immune checkpoint inhibitor.

In another aspect, provided is a method of initiating or enhancing the effectiveness (e.g., therapeutic efficacy) of a checkpoint inhibitor by administering to an individual a composition comprising an antibody that preferentially depletes regulatory B10 cells which, when administered in a combination therapy regimen with an immune checkpoint inhibitor, results in improvement, enhancement or enablement of the individual's response to the immune checkpoint inhibitor (as compared to a treatment regimen of administration of the immune checkpoint inhibitor alone (i.e., without administration of the antibody that preferentially depletes regulatory B10 cells in the same treatment regimen). The improved, enhanced or enabled response can be measured by, for example, increased activation of a T cell response (e.g., an anti-tumor immune response) or amelioration or inhibition of disease progression, which is intended to be therapeutically affected by the combination therapy regimen.

In another aspect, provided is a method for reducing the toxicity of an immune checkpoint inhibitor, or enabling therapeutic effects from the immune checkpoint inhibitor to be obtained with a lower dose, the method comprising administering to an individual a therapeutically effective amount of a composition comprising an antibody that preferentially depletes regulatory B10 cells and a therapeutically effective amount of a composition comprising an immune checkpoint inhibitor. This method may also be used to prolong the therapeutic effectiveness of an immune checkpoint inhibitor.

In a further aspect, provided is a method of treating cancer, or for promoting (one or more of initiating, enhancing, or prolonging) an anti-tumor immune response in an individual in need thereof (an individual with cancer), comprising administering to the individual a treatment regimen comprising a therapeutically effective amount of an antibody that preferentially depletes regulatory B10 cells and a therapeutically effective amount of an immune checkpoint inhibitor. An antibody that preferentially depletes human B10 cells may further comprise a pharmaceutically acceptable carrier. One or more immune checkpoint inhibitor therapies, used in the methods described herein, may also further comprise a pharmaceutically acceptable carrier.

Also provided herein is use of an antibody that preferentially depletes regulatory B10 cells, in treatment of a disease in which a T cell immune response is suppressed or inhibited, to promote or enhance T cell activation (e.g., $CD4^{+}$ T cells and/or $CD8^{+}$ T cells), or an anti-tumor response. The use may also comprise promoting or enhancing T cell activation, or an anti-tumor response induced by treatment with an immune checkpoint inhibitor. Provided herein is use of an antibody that preferentially depletes regulatory B10 cells in a therapy that inhibits immune checkpoint pathways to treat cancer.

In a further aspect, antibodies capable of binding to human CD22 and depleting B10 cells are also provided. These antibody comprises the VH selected from the group consisting of SEQ ID NO: 2, 3, 4, and 5 and sequences 90% identical to SEQ ID NO: 2, 3, 4, and 5 and the VL selected from the group consisting of SEQ ID NO: 15, 16, 19, and 20 and sequences 90% identical to SEQ ID NO: 15, 16, 19, and 20. An antibody that specifically binds to human CD22 comprising a heavy chain variable region and a light chain variable region, wherein the heavy chain variable region ("VH") comprises three complementarity determining regions, VH CDR1, VH CDR2, and VH CDR3 and the light chain variable region ("VL") comprises three complementarity determining regions, VL CDR1, VL CDR2, and VL CDR3, and wherein VH CDR1 is selected from the group consisting of SEQ ID NO: 27, 28 and sequences 90% identical to SEQ ID NO: 27 and 28; VH CDR2 is selected from the group consisting of SEQ ID NO: 29, 30 and 31 and sequences 90% identical to SEQ ID NO: 29, 30, and 31; VH CDR3 is selected from the group consisting of SEQ ID NO: 32 and 33 and sequences 90% identical to SEQ ID NO: 32 and 33; VL CDR1 is selected from the group consisting of SEQ ID NO:34, 37, 40, 43 and sequences 90% identical to SEQ ID NO: 34, 37, 40, 43; VL CDR2 is selected from the group consisting of SEQ ID NO: 35, 38, 41 and 44 and sequences 90% identical to SEQ ID NO: 35, 38, 41 and 44; and VL CDR3 is selected from the group consisting of SEQ ID NO: 36, 39, 42 and 45 and sequences 90% identical to SEQ ID NO: 36, 39, 42, and 45. The various VH and VL chains described herein may be used in various combinations and may be provided in chimeric or humanized form. Suitably the antibodies are capable of inducing homotypic adhesion.

Other aspects, objects and features of the invention will be apparent from the following description.

BRIEF DESCRIPTION OF THE DRAWINGS

FIG. 14A shows CD25$^+$FoxP3$^+$CD4$^+$ Treg cells in treated and tumor-bearing mice. Mice were treated with MB22-10 or control (CTRL) mAb on days −7, 0, and 7, PD-1 mAb on days 1, 4, 7 and 10, and/or CTLA-4 mAb on days 1, 4, and 7, with MC38 cells (2×10$^6$) implanted on day 0 in some mice as indicated.

Tumor-draining lymph node and spleen lymphocytes were assessed on day 14 by immunofluorescence staining with flow cytometry analysis. Histograms show CD25$^+$FoxP3$^+$CD4$^+$ Treg cell frequencies within the indicated gates for representative control (left panels) and tumor-bearing (right panels) mice. Numbers (±SEM) are group means. The graphs show cell numbers for individual mice, with horizontal bars indicating group means from 2-3 pooled experiments (n=6-12 mice per group). FIG. 14B shows MB22-10 mAb and Ontak independently deplete B10 cells and Treg cells in mice with tumors, respectively. CD25$^+$FoxP3$^+$CD4$^+$ Treg cell and B10 cell numbers within the tumor-draining lymph nodes and spleens of mice with tumors as in were quantified 9 days after MB22-10 or control mAb and/or Ontak treatments were initiated. Horizontal bars indicate mean cell numbers from 1 experiment (n=4 mice per group). FIG. 14C shows MB22-10 mAb plus Ontak treatments inhibit tumor growth. Tumors (0.03-0.10 cm$^3$) were initiated 6-9 days before MB22-10 or control mAb treatments on days 0, 6, and 12, PD-1 mAb on days 0, 3, 6, 9, and/or Ontak treatment on days 0, 3, and 6. Spider plots of individual mice pooled from 3-9 independent experiments (n=10-32 total mice per group) are shown. The mean days for tumors to reach a size of 0.5 cm$^3$ (MT$_{0.5}$) are indicated for each treatment group. In FIG. 14A-C significant differences between each of the indicated treatment groups and the control mAb-treated groups are shown: *, p<0.05, , p<0.01, *, p<0.001, ****, p<0.0001.

FIG. 15A shows CD25$^+$FoxP3$^+$CD4$^+$ Treg cell and FIG. 15B shows B10 cell numbers within the tumor-draining lymph nodes and spleens of mice with MC38 tumors were quantified 9 days after MB22-10 or control mAb and/or Ontak treatments were initiated as in FIG. 14. Horizontal bars indicate mean cell numbers from 1 experiment (n=4 mice per group). Significant differences between control and treatment groups are indicated: *, p<0.05; , p<0.01; *, p<0.001.

FIG. 16A shows representative flow cytometry dot plots showing IL-10 expression by single viable CD19$^+$ B cells. Numbers indicate the mean frequencies of B cells within the indicated gates. FIG. 16B shows scatter plots showing mean B10 cell frequencies and numbers for individual mice, with 6-10 mice per group pooled from 3 to 4 independent experiments. Bars indicate means. Significant differences between group means are indicated: *, p<0.05; **, p<0.01.

FIG. 17A shows representative flow cytometry dot plots showing single viable B220$^+$ B cell frequencies among lymphocytes, with numbers indicating mean B cell frequencies within the indicated gates. FIG. 17B shows scatter plots showing mean B cell frequencies and numbers for individual mice, with 6-10 mice per group pooled from 3 to 4 independent experiments. Bars indicate means with significant differences between group means indicated: *, p<0.05; **, p<0.01.

FIG. 18A shows representative flow cytometry histograms showing single viable CD1d$^{hi}$CD21$^{hi}$ or CD1d$^{hi}$CD5$^+$ B cell frequencies among lymphocytes, with numbers indicating mean cell frequencies within the indicated gates. FIG. 18B shows scatter plots showing mean cell frequencies for individual mice, with 6-10 mice per group pooled from 3 to 4 independent experiments. Bars indicate means with significant differences between group means indicated: *** p<0.001.

FIG. 19A supplies representative flow cytometry dot plots showing single viable B220$^+$ B cell frequencies among lymphocytes, with numbers indicating cell frequencies within the indicated gates. FIG. 19B shows scatter plots showing mean B220$^+$ B cell frequencies for individual mice, with 6-10 mice per group pooled from 3 to 4 independent experiments. Bars indicate means, with significant differences between group means indicated: *, p<0.05; **, p<0.01.

FIG. 20A shows representative flow cytometry histograms showing single viable B220$^+$ B cell staining intensities in HB22 mAb-treated mice relative to B cells from control mAb-treated mice. FIG. 20B shows scatter plots showing mean B220$^+$ B cell staining (mean fluorescence intensity) for IgG1 on a linear scale for individual mice, with 6-10 mice per group pooled from 3 to 4 independent experiments. Bars indicate means, with significant differences between group means indicated: , p<0.01; *, p<0.001.

FIG. 21A shows representative flow cytometry histograms showing single viable $CD19^+$ B cell staining intensities in HB mAb-treated mice relative to B cells from control mAb-treated mice. FIG. 21B shows scatter plots showing mean $CD19^+$ B cell staining (mean fluorescence intensity) on a linear scale for individual mice, with 6-10 mice per group pooled from 3 to 4 independent experiments. Bars indicate means, with significant differences between group means indicated: , $p<0.01$; *, $p<0.001$.

FIG. 22 shows a sequence alignment of the variable heavy and variable light chains of the indicated antibodies and shows the CDRs of each chain in gray and provides the reference to the SEQ ID NO: for each sequence.

DETAILED DESCRIPTION OF THE INVENTION

Figure 1:
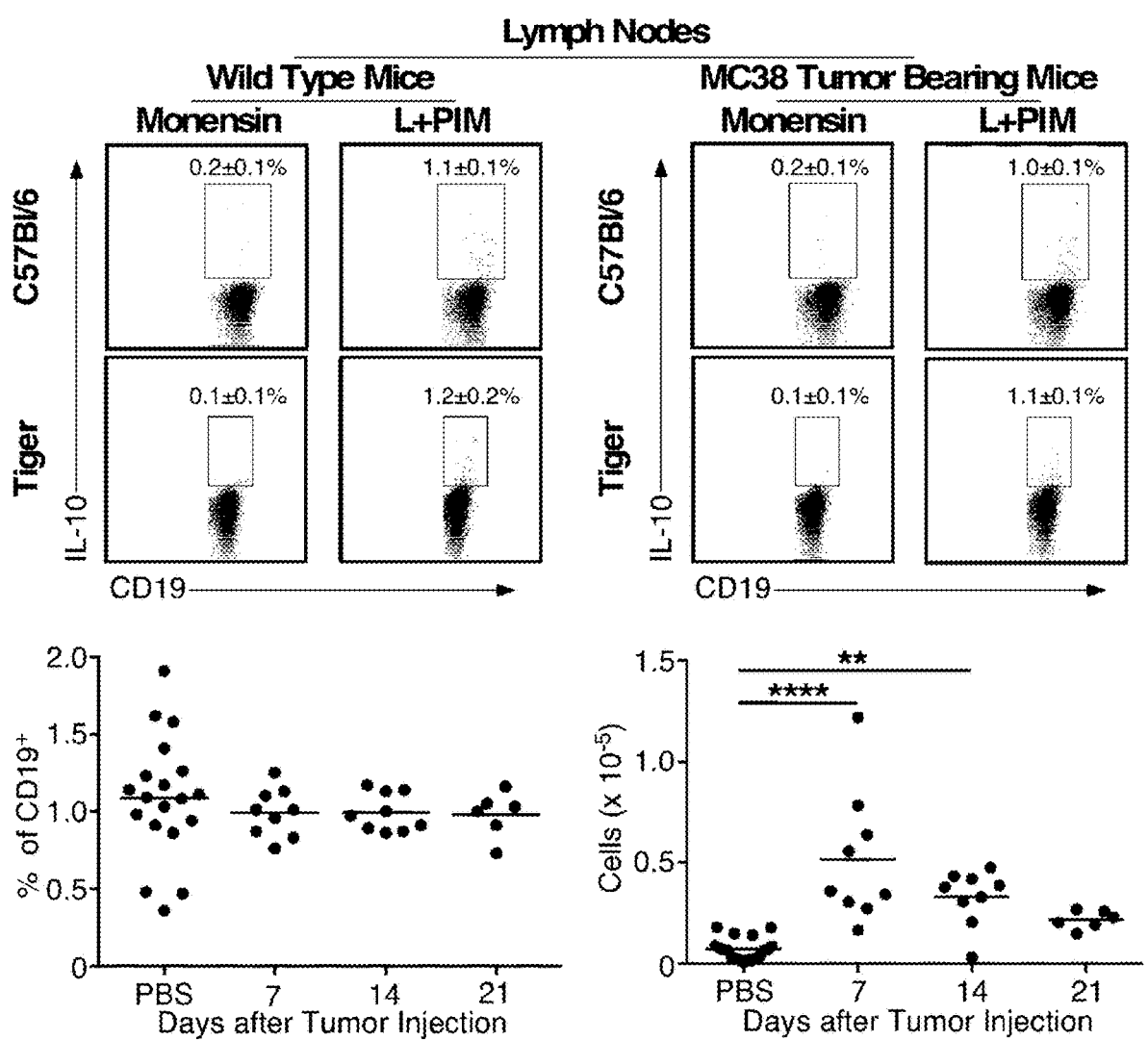
FIGS. 1 & 2 are graphs showing B10 cell numbers expand during MC38 tumor-induced inflammation in mice. IL-10 competent B10 cells within inguinal lymph nodes (FIG. 1) and spleen (FIG. 2) were quantified before and 7, 14 and 21 days after mice were given either subcutaneous MC38 tumor cells ($2\times10^6$) or PBS on day 0. On the indicated days, tissue lymphocytes were purified and cultured with monensin alone or stimulated ex vivo with LPS, PMA, ionomycin, and monensin (L+PIM) for 5 h. Wild type lymphocytes were stained for cell surface CD19 and intracellular IL-10 to quantify B10 cell frequencies, while lymphocytes from Tiger mice were stained for CD19 with cytoplasmic GFP expression assessed by flow cytometry. Representative flow cytometry histograms show IL-10 expression by single viable $CD19^+$ B cells. Lymphocytes cultured with monensin alone served as negative staining controls (Matsushita, Tedder TF. Identifying regulatory B cells (B10 cells) that produce IL-10 in mice. *Methods Mol Biol.* 2011; 677:99-111). Numbers indicate the frequencies (mean±SEM) of cells within the indicated gates for all mice tested. Data from PBS-treated mice were not significantly different between time points (d 7, 14, and 21) and were therefore pooled. Scatter plots show mean B10 cell frequencies and numbers for individual mice, with 6-19 mice per group. Bars indicate means. Significant differences between group means are indicated: *, p<0.05; , p<0.01, **, p<0.0001.

While the terms used in the description of the invention are believed to be well understood by one of ordinary skill in the pharmaceutical arts, definitions, where provided herein, are set forth to facilitate description of the invention, and to provide illustrative examples for use of the terms.

As used herein, the terms "a", "an", and "the" mean "one or more", unless the singular is expressly specified (e.g., singular is expressly specified, for example, in the phrase "a single formulation").

As used herein, "preferentially depletes", in relation to the activity of an antibody used in the invention means that the antibody selectively kills, inhibits the function of, or otherwise functionally alters or compromises B10 cell regulatory activity directed towards target immune cells (e.g., T cells or antigen-presenting cells) during an immune response. Moreover, the antibody preferentially depletes significantly more B10 cells as compared to most other B cell subpopulations as a result of treatment with such antibody. For example, an antibody that preferentially depletes B10 cells, when used in treatment, will preferentially deplete at least 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of B10 cells from the B cell population treated, while at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of most other subpopulations of the B cell population treated are left intact (in terms of one or more of function, activity, proportion, or relative number). As used herein, "enhances or improves or prolongs", in relation to a therapeutic effect contributed by addition of an antibody that preferentially depletes regulatory B10 cells to a treatment regimen using an immune checkpoint inhibitor, refers to an improvement in the therapeutic effect measured. For example, the enhancement or improvement may be measured by a clinical outcome (e.g., reduction in tumor size or progression) or a measure of an immune response (e.g., activation of $CD4^+$ T cells and/or $CD8^+$ T cells, or duration of anti-tumor response) as a result of the addition of an antibody that preferentially depletes regulatory B10 cells to the treatment regimen as compared to treatment without such addition (e.g., treatment with one or more immune checkpoint inhibitors alone), wherein a measured response is improved by 5%, 10%, 15%, 20%, 25%, 30%, 35%, 40%, 45%, 50%, 55%, 60%, 65%, 70%, 75%, 80%, 85%, 90%, 95%, 98% or more.

The terms "first" and "second" are used herein for purposes of distinguishing between two compounds, or between two compositions, as will be clearer from the description.

The phrase "therapeutically effective amount" means an amount of a composition or combination that results in a therapeutic effect following administration to an individual in need of such composition or combination. In immunotherapy, the therapeutic effect may be represented by activation of a T cell response that is suppressed prior to treatment with a method described herein. Such activation may be measured by an increase in one or more T cell subpopulations (e.g., $CD4^+$ T cells, $CD8^+$ T cells) using methods known in the art (e.g., labeling with detectable markers followed by flow cytometry analyses) or of the induced or increased expression of activation markers for such T cell subpopulations (e.g., increased CD44 or decreased CD62L expression). Alternatively, activation may also be measured by a decrease in the number or function of regulatory T cells (e.g., $CD25^+FoxP3^+$, $CD4^+$ cells). Thus, in one aspect, therapeutic efficacy may be assessed by clinical outcome; an increase in the number of anti-tumor T cells or activated T cells as compared with the number prior to treatment or in absence of treatment with a combination of an antibody that preferentially depletes regulatory B10 cells and an immune checkpoint inhibitor.

In treatment of cancer, a therapeutic effect may include but is not limited to, one or more of (a) an immune-related response, as known to those skilled in the art as an immune-related complete response or an immune-related partial response relative to total tumor burden (e.g., an anti-tumor immune response); and (b) traditional overall objective response rate using the appropriate response assessment criteria known to those skilled in the art and depending on the type of cancer treated (e.g., for lymphoma, see Cheson et al., 2014, *J. Clin. Oncology* 32 (27):3059-3067; for solid nonlymphoid tumors, Response Evaluation Criteria In Solid Tumors (RECIST)) (e.g., an antitumor response).

The term "pharmaceutically acceptable carrier" is used herein to mean any compound or composition or carrier medium useful in any one or more of administration, delivery, storage, stability of a composition or combination described herein. These carriers are known in the art to include, but are not limited to, a diluent, water, saline, suitable vehicle (e.g., liposome, microparticle, nanoparticle, emulsion, capsule), buffer, medical parenteral vehicle, excipient, aqueous solution, suspension, solvent, emulsions, detergent, chelating agent, solubilizing agent, salt, colorant, polymer, hydrogel, surfactant, emulsifier, adjuvant, filler, preservative, stabilizer, oil, binder, disintegrant, absorbant, flavor agent, and the like as broadly known in the pharmaceutical art.

The terms "specifically binds", or "binding specificity" are used alternatively and in relation to an antibody, refers to the ability of the antibody to form one or more noncovalent bonds with an antigen used to induce formation of the antibody (e.g., antigens exemplified herein include CD20, CD22, PD-1, PD-L1, CTLA-4), by noncovalent interactions between an antibody combining site and the antigen.

The term "identity", as recognized by those skilled in the art, represents a comparison between two or more amino acid sequences performed using published methods and software known in the art. For example, the compared amino acid sequences are optimally aligned, and the number of amino acid differences are counted and converted to a percentage. For example, if a first amino acid sequence of 50 amino acids is optimally aligned with a second amino acid sequence of 50 amino acids, and 5 out of 50 amino acids differ from the second amino acid sequence, then the first amino acid sequence is said to have 10% identity with the second amino acid sequence.

The term "antibody" refers to a full-length antibody, derivatives or fragments of full length antibodies that comprise less than the full length sequence of the antibody but retain at least the binding specificity of the full length antibody (e.g., variable portions of the light chain and heavy chain), chimeric antibodies, humanized antibodies, synthetic antibodies, recombinantly produced antibodies, as known to those skilled in the art, and produced using methods known in the art. Examples of antibody fragments include, but are not limited to, Fab, Fab', F(ab')$_2$, scFv, Fv, dimeric scFv, Fd, and Fd. Fragments may be synthesized or generated by enzymatic cleavage using methods known in the art. Antibodies can also be produced in either prokaryotic or eukaryotic in vitro translation systems using methods known in the art. Antibodies may also be referred to herein by their complementarity-determining regions (CDRs), part of the variable chains in antibodies that bind to their specific antigen. Thus, an antibody may be referred to herein by its CDRs of the heavy chain ($V_H$ CDR 1, $V_H$ CDR 2, and $V_H$ CDR 3), and the light chain ($V_L$ CDR 1, $V_L$ CDR 2, and $V_L$ CDR 3) for illustrative purposes. Likewise, an antibody of an IgG class may be referred to by its subclass (e.g., IgG1, IgG2, IgG3, and IgG4). Amino acid sequences are known to those skilled in the art for the Fc portion of antibodies of the respective IgG subclass.

Antibodies herein specifically include "chimeric" antibodies (immunoglobulins), as well as fragments of such antibodies, as long as they exhibit the desired biological activity (U.S. Pat. No. 4,816,567; Morrison et al., Proc. Natl. Acad. Sci. USA 81:6851-6855 (1984); Oi et al., Biotechnologies 4(3):214-221 (1986); and Liu et al., Proc. Natl. Acad. Sci. USA 84:3439-43 (1987)).

"Humanized" or "CDR grafted" forms of non-human (e.g., murine) antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. The term "hypervariable region" when used herein refers to the amino acid residues of an antibody which are associated with its binding to antigen. The hypervariable regions encompass the amino acid residues of the "complementarity determining regions" or "CDRs". In some instances, framework region (FW) residues of the human immunoglobulin are also replaced by corresponding non-human residues (so called "back mutations"). Furthermore, humanized antibodies may be modified to comprise residues which are not found in the recipient antibody or in the donor antibody, in order to further improve antibody properties, such as affinity. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); and Reichmann et al., Nature 332:323-329 (1988).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger el al., Proc. Natl. Acad. Sci. USA 90:6444-6448 (1993).

The expression "linear antibodies" when used throughout this application refers to the antibodies described in Zapata, et al. Protein Eng. 8(10): 1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

The terms "treat", "treating", or "treatment" as used herein, embrace one or more of preventative (prophylactically) or therapeutically (palliative).

The term "cancer" is used herein to refer to all types of cancer, neoplasm or malignant tumors found in mammals (e.g., humans), including leukemias, lymphomas, carcinomas and sarcomas. Exemplary cancers that may be treated with a composition, combination or method provided herein include solid, non-lymphoid tumors, B cell leukemias, Non-Hodgkin's Lymphoma, and multiple myeloma.

The term "solid, non-lymphoid tumor" is used herein, for purposes of the specification and claims, to mean any primary tumor of epithelial cell origin, including tumors originating in an organ or gland such as liver, lung, brain, adrenal gland, breast, colon, bladder, pancreas, stomach, prostate, gastrointestinal tract, or reproductive tract (cervix, ovaries, endometrium etc.), or metastases thereof. For the purposes of the present invention, "solid, non-lymphoid tumor" also includes melanoma.

The term "individual" is used herein to refer to a mammal, preferably a human; and more preferably, a human in need of treatment with either an antibody that preferentially depletes B10 cells in a human, or a combination of such antibody with an immune checkpoint inhibitor. The term individual may be used interchangeably with subject and/or patient.

The term "immune checkpoint inhibitor" refers to a molecule, compound, or composition that binds to an immune checkpoint protein and blocks its activity and/or inhibits the function of the immune regulatory cell expressing the immune checkpoint protein that it binds (e.g., Treg cells, tumor-associated macrophages, etc.). Immune checkpoint proteins may include, but are not limited to, CTLA4 (Cytotoxic T-Lymphocyte-Associated protein 4, CD152), PD1 (also known as PD-1; Programmed Death 1 receptor), PD-L1, PD-L2, LAG-3 (Lymphocyte Activation Gene-3), OX40, A2AR (Adenosine A2A receptor), B7-H3 (CD276), B7-H4 (VTCN1), BTLA (B and T Lymphocyte Attenuator, CD272), IDO (Indoleamine 2,3-dioxygenase), KIR (Killer-cell Immunoglobulin-like Receptor), TIM 3 (T-cell Immunoglobulin domain and Mucin domain 3), VISTA (V-domain Ig suppressor of T cell activation), and IL-2R (interleukin-2 receptor).

Immune checkpoint inhibitors are well known in the art and are commercially or clinically available. These include but are not limited to antibodies that inhibit immune checkpoint proteins. Illustrative examples of checkpoint inhibitors, referenced by their target immune checkpoint protein, are provided as follows. Immune checkpoint inhibitors comprising a CTLA-4 inhibitor include, but are not limited to, tremelimumab, and ipilimumab (marketed as Yervoy). Immune checkpoint inhibitors comprising a PD-1 inhibitor include, but are not limited to, nivolumab (BMS-936558/MDX-1106, Bristol-Myers Squibb), pidilizumab (CureTech), AMP-514 (MedImmune), pembrolizumab (Merck), AUNP 12 (peptide, Aurigene and Pierre). Immune checkpoint inhibitors comprising a PD-L1 inhibitor include, but are not limited to, BMS-936559/MDX-1105 (Bristol-Myers Squibb), MPDL3280A (Genentech), MED14736 (MedImmune), MSB0010718C (EMD Sereno). Immune checkpoint inhibitors comprising a B7-H3 inhibitor include, but are not limited to, MGA271 (Macrogenics). Immune checkpoint inhibitors comprising an LAG3 inhibitor include, but are not limited to, IMP321 (Immuntep), BMS-986016 (Bristol-Myers Squibb). Immune checkpoint inhibitors comprising a KIR inhibitor include, but are not limited to, IPH2101 (Iirilumab, Bristol-Myers Squibb). Immune checkpoint inhibitors comprising an OX40 inhibitor include, but are not limited to MEDI-6469 (MedImmune). An immune checkpoint inhibitor targeting IL-2R, for preferentially depleting Treg cells (e.g., FoxP-3$^+$ CD4$^+$ cells), comprises IL-2-toxin fusion proteins, which include, but are not limited to, denileukin diftitox (Ontak; Eisai).

The term "an antibody that preferentially depletes B10 cells" is used herein to refer to a subset of antibodies that specifically bind to either CD20 or CD22 and that preferentially depletes B10 cells. It appears that the ability of this subset of antibodies that preferentially deplete B10 cells involves one or more factors that may include, but are not limited to, where it binds on CD22 or CD20 (e.g., distance from cell surface, such that antibody dependent cellular cytotoxicity is inefficient or not detectable), affinity, avidity, ability to crosslink target molecules, isotype of the antibody, and ability to transmit or inhibit cellular signals that result in antigen internalization and result in B10 cell depletion. Such antibody may also be engineered using methods known in the art for modifying the Fc portion (e.g., deletion or substitution of amino acids) such that it is unable to bind, or is inefficient in binding to, the Fc receptor of immune effector cells expressing Fc receptors. An antibody that preferentially depletes B10 cells may be non-naturally occurring in the sense that immunization in vitro or in an in vivo animal model system is necessary for producing antibodies, followed by selective screening for antibody binding specificity, and the ability to preferentially deplete B10 cells, using methods known in the art. In this case, one would not expect a human individual to harbor naturally occurring antibodies that preferentially deplete B10 cells because of clonal deletion. Illustrated in Examples 2-6 and FIGS. 1-15 are illustrative examples of an antibody that preferentially deplete B10 cells, designated MB22-10. The MB22-10 antibodies are described in Horikawa et al., J Immunol 2013 vol 190: 1158-1168; in Haas et al., J. Immunology, 2006, 177:3063-3073; in Poe et al. PLoS One 2011 6:e22464; and in Matsushita et al., J Immunology 2010 185:2240-2252. The ability of an antibody to mediate homotypic adhesion (cellular aggregation), via generation of transmembrane signals following antibody binding to CD22 or CD20, can also be used as a surrogate marker for screening for antibodies that preferentially deplete B10 cells. In that regard, shown in Example 1 is use of B cell homotypic adhesion as a marker for antibodies that preferentially deplete B10 cells. In using such a marker, an example of an antibody that can bind to human CD20 and preferentially deplete human B10 cells includes an antibody comprised of the CDRs of rutuximab with either an Fc portion of an IgG4 Ab or an FC portion which has been engineered to neither activate complement nor participate in antibody-dependent cell-mediated cytotoxicity (ADCC). In using such a marker, an example of an antibody that can bind to human CD20 and preferentially deplete human B10 cells includes an antibody comprised of the CDRs of tositumomab with either an Fc portion of an IgG4 Ab or an Fc region which has been engineered to neither activate complement nor participate in antibody-dependent cell-mediated cytotoxicity (ADCC). Rutuximab and tositumomab are antibodies well known and well characterized by those skilled in the art.

Methods for treating cancer or initiating, enhancing, or prolonging an anti-tumor response in an individual are provided herein. The methods may include administering an antibody preferentially depleting B10 cells to a subject to treat a solid, non-lymphoid tumor. In another embodiment, the method includes administering an antibody preferentially depleting B10 cells and an immune checkpoint inhibitor to any individual suffering from cancer or a tumor. The antibody preferentially depleting B10 cells and the immune checkpoint inhibitor combination may be administered in any way. They may be administered as separate administrations in an administration regimen in which the combination is administered separately to the individual with a time course of administration best suited to each of the components as was done in the Examples. Alternatively, the combination may be administered as a unitary composition. Those skilled in the art can develop the combination therapy regimen.

Methods of initiating, enhancing, or prolonging T cell activation in an individual in need thereof comprising administering an antibody preferentially depleting B10 cells and an immune checkpoint inhibitor are also provided. The methods may also be completed by any means and may use more than one composition or a unitary composition comprising both therapeutic agents.

Methods of initiating or enhancing or prolonging effectiveness of an immune checkpoint inhibitor, or enabling toxicity or dose of an immune checkpoint inhibitor to be reduced are also provided. The methods include administering to an individual a composition comprising an antibody that preferentially depletes B10 cells in a combination therapy regimen with a composition comprising an immune checkpoint inhibitor.

Methods of treating a disease ameliorated by stimulation of an immune response are also provided. These methods include administering to an individual in need thereof a composition comprising an antibody that preferentially depletes B10 cells and further a composition comprising an immune checkpoint inhibitor.

In the methods described herein the antibody that preferentially depletes B10 cells may be selected from antibody includes the CDR portions of an antibody selected from the group consisting of MB22-10, MB22-103, MB22-106, MB22-107, MB22-115, rutuximab, and tositumomab or any of the combinations described herein. The antibody that preferentially depletes B10 cells suitably induces homotypic adhesion of B cells.

In any of the methods of treatment provided herein, the dosage of an antibody or combination will depend on such factors as the mode of administration, the formulation for administration, type of cancer, stage of cancer, the size and health of the individual to receive such a composition, and other factors which can be taken into consideration by a medical practitioner whom is skilled in the art of determining appropriate dosages for treatment. For example, for methods of treatment provided herein, an antibody that preferentially depletes B10 cells or an immune checkpoint inhibitor may be administered in a dosage range (per body weight of the individual) that is between about 0.1 mg/kg to about 50 mg/kg, about 0.5 mg/kg to about 20 mg/kg, about 0.5 mg/kg to about 10 mg/kg, about 0.5 mg/kg to about 5 mg/kg, or 0.5 mg/kg to about 1 mg/kg. One skilled in the art can apply known principles and models of drug delivery and pharmacokinetics to ascertain a likely range of dosages to be tested in preclinical and clinical studies for determining a therapeutically effective amount of a composition or combination used in the methods of treatment provided herein. A composition or combination, useful in a method of treatment provided herein, may further comprise a pharmaceutically acceptable carrier to facilitate one or more of storage, stability, administration, and delivery. The carrier may be particulate, so that the composition or combination may be in, for example, powder or solid form. The carrier may be in a semi-solid, gel, or liquid formula, so that the composition or combination may be injected, applied, or otherwise administered. The mode of administration of a composition or combination, useful in a method of treatment provided herein, to an individual (such as a human) in need of thereof may be any mode known in the art to be suitable for delivering a pharmaceutical composition, and particularly suitable for treating cancer. A mode of administration may include but is not limited to, intravenously, intraperitoneally, subcutaneously, intramuscularly, by perfusion, and by peristaltic techniques. A composition or combination, useful in a method of treatment provided herein, may also be combined with other cancer treatments known to those skilled in the art, including but not limited to chemotherapeutic treatment and radiation therapies.

The frequency, order of administration, doses and dosage regimen of combination therapy can be determined by a physician, taking into account the medical literature, the health, age and sex of the individual, the disease or condition or disorder to be treated, the mode of administration and dosing schedule of the composition or combination or therapy, and other relevant considerations. In a method of treatment provided herein, an immune checkpoint inhibitor may be administered to an individual at a suitable frequency to be therapeutically effective. For example, an immune checkpoint inhibitor may be administered twice weekly, once each week, once every 2 weeks, once every 3 weeks, once each month, once every two months, once every 3 months, once every 4 months, once every 5 months, or once every 6 months. In a method of treatment provided herein, an antibody preferentially depleting B10 cells may be administered to an individual at a suitable frequency to be therapeutically effective. For example, an antibody preferentially depleting B10 cells may be administered once, administered at the same frequency as an immune checkpoint inhibitor, or administered at a different frequency as an immune checkpoint inhibitor. In a method of treatment using a combination provided herein, in one example, administration of an immune checkpoint inhibitor is preceded by administration of an antibody preferentially depleting B10 cells. In another example of a method of treatment using a combination provided herein, administration of an immune checkpoint inhibitor is followed by administration of an antibody preferentially depleting B10 cells.

Antibodies capable of preferentially depleting human B10 cells are also provided. An antibody that specifically binds to human CD22 may comprise a heavy chain variable region and a light chain variable region, wherein the heavy chain variable region ("VH") comprises three complementarity determining regions, VH CDR1, VH CDR2, and VH CDR3 and the light chain variable region ("VL") comprises three complementarity determining regions, VL CDR1, VL CDR2, and VL CDR3, and wherein VH CDR1 is selected from the group consisting of SEQ ID NO: 27, 28 and sequences 80%, 85%, 90%, 92%, 95%, 96%, 97%, 98% identical to SEQ ID NO: 27 and 28; VH CDR2 is selected from the group consisting of SEQ ID NO: 29, 30 and 31 and sequences 80%, 85%, 90%, 92%, 95%, 96%, 97%, 98% identical to SEQ ID NO: 29, 30, and 31; VH CDR3 is selected from the group consisting of SEQ ID NO: 32 and 33 and sequences 80%, 85%, 90%, 92%, 95%, 96%, 97%, 98% identical to SEQ ID NO: 32 and 33; VL CDR1 is selected from the group consisting of SEQ ID NO:34, 37, 40, 43 and sequences 80%, 85%, 90%, 92%, 95%, 96%, 97%, 98% identical to SEQ ID NO: 34, 37, 40, 43; VL CDR2 is selected from the group consisting of SEQ ID NO: 35, 38, 41 and 44 and sequences 80%, 85%, 90%, 92%, 95%, 96%, 97%, 98% identical to SEQ ID NO: 35, 38, 41 and 44; and VL CDR3 is selected from the group consisting of SEQ ID NO: 36, 39, 42 and 45 and sequences 80%, 85%, 90%, 92%, 95%, 96%, 97%, 98% identical to SEQ ID NO: 36, 39, 42, and 45. These CDRs may be used to generate humanized antibodies by combination with FW regions and constant regions of human antibodies to generate human CD22 specific humanized antibodies. The CDRs are placed within FW regions such that the heavy chain variable region ("VH") which comprises three complementarity determining regions, VH CDR1, VH CDR2, and VH CDR3, and four framework regions, VH FW1, VH FW2, VH FW3, and VH FW4, are present in the order VH FW1-VH CDR1-VH FW2-VH CDR2-VH FW3-VH CDR3-VH FW4 and the light chain variable region ("VL") which also comprises three complementarity determining regions, VL CDR1, VL CDR2, and VL CDR3, and four framework regions, VL FW1, VL FW2, VL FW3, and VL FW4, are present in the order VL FW1-VL CDR1-VL FW2-VL CDR2-VL FW3-VL CDR3-VL FW4. Those skilled in the art are capable of generating humanized antibodies based on the CD22 specific CDRs or heavy and light chain variable regions provided herein.

In one embodiment, the antibody comprises the VH CDRs of SEQ ID NOs: 27, 29, and 32 and the VL CDRs of SEQ ID NOs: 40, 41 and 42 (HB22-103) or sequences having 80%, 85%, 90%, 92%, 95%, 96%, 97%, 98% identity to these sequences. In one embodiment, the antibody comprises the VH CDRs of SEQ ID NOs: 27, 30, and 32 and the VL CDRs of SEQ ID NOs: 37, 38 and 39 (HB22-106) or sequences having 80%, 85%, 90%, 92%, 95%, 96%, 97%, 98% identity to these sequences. In one embodiment, the antibody comprises the VH CDRs of SEQ ID NOs: 28, 31, and 33 and the VL CDRs of SEQ ID NOs: 34, 35 and 36 (HB22-107) or sequences having 80%, 85%, 90%, 92%, 95%, 96%, 97%, 98% identity to these sequences. In yet another embodiment, the antibody comprises the VH CDRs of SEQ ID NOs: 27, 30, and 32 and the VL CDRs of SEQ ID NOs: 43, 44 and 45 (HB22-115) or sequences having 80%, 85%, 90%, 92%, 95%, 96%, 97%, 98% identity to these sequences. In still another embodiment, the antibody comprises the VH selected from the group consisting of SEQ ID NO: 2, 3, 4, and 5 and sequences 80%, 85%, 90%, 92%, 95%, 96%, 97%, 98% identical to SEQ ID NO: 2, 3, 4, and 5 and the VL selected from the group consisting of SEQ ID NO: 15, 16, 19, and 20 and sequences 80%, 85%, 90%, 92%, 95%, 96%, 97%, 98% identical to SEQ ID NO: 15, 16, 19, and 20. Suitably the antibody includes SEQ ID NO: 2 and 19. The antibody may include SEQ ID NO: 3 and 16. The antibody may include SEQ ID NO: 4 and 20. The antibody may include SEQ ID NO: 5 and 15. The various heavy and light chain sequences and the various CDRs identified in the current application may be used interchangeably as these antibodies are all directed to the same epitope on human CD22. We have demonstrated that the VH and VL may be used interchangeably and we expect that the CDRs will be likewise interchangeable between these identified antibodies.

The sequences provided are only for the variable regions of the antibody. Those skilled in the art will appreciate that these regions determine the specificity of the antibody but that the effector function of the antibody is generally dependent on the constant regions (and the specific isotype) of the antibody. Those skilled in the art can engineer antibodies for specific purposes based on the variable regions provided herein. As described in the Examples, antibodies capable of preferentially depleting B10 cells are generally antibodies capable of inducing homotypic adhesion of the B10 cells. In some embodiments, the antibody comprises an Fc portion of a human or humanized IgG4 antibody. In some embodiments, the antibody comprises an Fc region which has been engineered to neither activate complement nor participate in antibody-dependent cell-mediated cytotoxicity (ADCC).

The antibodies capable of binding CD22 described herein may be used as the antibody preferentially depleting B10 cells in any of the methods described herein.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Example 1

This Example demonstrates use of an in vitro surrogate marker for screening or identifying antibodies that preferentially deplete B10 cells, rather than having to perform in vivo experiments to identify and demonstrate preferential depletion of B10 cells. In this example, the binding of select CD20 antibodies or CD22 antibodies to their respective human cell surface receptors has the ability to induce rapid and potent homotypic adhesion in murine B cells and human B cells through Fcγ receptor-independent signaling pathways. An assay for assessing an antibody's ability to induce homotypic adhesion was performed as described previously (Kansas and Tedder, 1991, *J. Immunol.*, 147(12):4094-4102). Briefly, cells were washed in cell culture medium containing 10% fetal calf serum, and 0.5 ml containing $5\times10^6$ cells was added into a 15 ml round bottom tube. Antibody that was to be screened was then added at concentrations 5- to 10-fold in excess of those required for saturation of the cell receptor (e.g., CD20 or CD22) as determined by indirect immunofluorescence staining with flow cytometry analysis. The cells and antibody were vortexed, and 0.1 ml of each treated cell suspension was placed in wells of a flat-bottom 96-well plate. The plate was then incubated at 37 degrees C. for 1 to 2 hours. Semi-quantitative scoring of cellular homotypic adhesion was made using the following criteria: "0" means that there was no homotypic adhesion (>90% of the cells were unaggregated); "+" means that the majority of cells are unaggregated but a few clusters of 10-20 cells were observed; "++" means that approximately 50% of cells were in medium-sized aggregates with the remainder as single cells; "+++" means that nearly all cells were in medium-to-large aggregates with less than 20% unaggregated cells; and "++++" means that greater than 90% of cells were in large aggregates. As shown in Table 1, the antibody that preferentially depletes B10 cells as illustrated in the examples herein, MB22-10, demonstrated semi-quantitative scores of approximately ++, depending on the B cell line used. MB22-10 is a mouse CD22 specific antibody. Also shown in Table 1 is tositumomab, which demonstrated a semi-quantitative score of +++ and ++++, depending on the B cell line used, whereas rituximab demonstrated a semi-quantitative score of approximately ++. Thus, tositumomab and rituximab, with the ability to generate Fc gamma receptor-independent signals that result in B cell homotypic adhesion, will also have the ability to deplete B10 cells through molecular pathways that are induced by B10 cell-depleting CD22 antibodies such as MB22-10.

TABLE 1

| B Cell receptor | Antibody | Score/B cell line 1 | Score/B cell line 2 |
| --- | --- | --- | --- |
| CD22 | MB22-10 | + | ++ |
| CD20 | tositumomab | +++ | ++++ |
| CD20 | rituximab | +/++ | ++ |

Example 2

Figure 2:
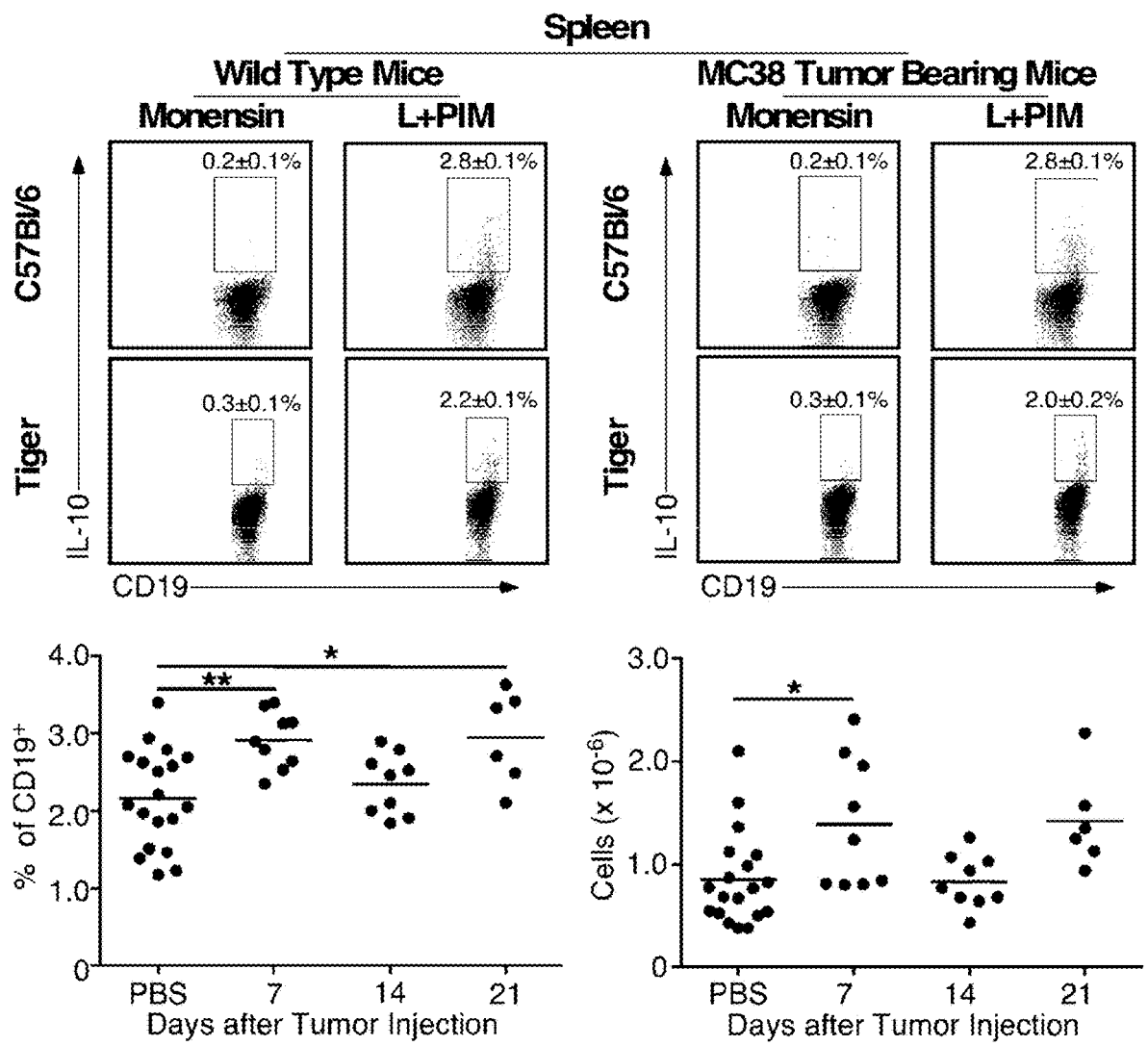

In this Example, shown in a standard animal model, is a method of immunotherapy and a method of treating cancer by administering an antibody that preferentially depletes B10 cells as a monotherapy. C57BL/6 mice were injected subcutaneously in the shaved back flank on day 0 with $2 \times 10^6$ MC38 (colon adenocarcinoma) tumor cells in 200 µl of PBS. On the indicated days, tissue lymphocytes were purified and cultured with monensin alone or stimulated ex vivo with LPS, PMA, ionomycin, and monensin (L+PIM) for 5 h. Wild type lymphocytes were stained for cell surface CD19 and intracellular IL-10 to quantify B10 cell frequencies, while lymphocytes from Tiger mice were stained for CD19 with cytoplasmic GFP expression assessed by flow cytometry. Representative flow cytometry histograms show IL-10 expression by single viable CD19$^+$ B cells in lymph nodes (FIG. 1) and spleen (FIG. 2). The scatter plots on the left in FIGS. 1 and 2 show that the relative frequency of B10 cells as a proportion of total B cells was not altered in the draining lymph nodes of tumor bearing mice, but were significantly increased in the spleens of mice with tumors. The scatter plots on the right show that the total numbers of B10 cells in the draining lymph nodes and spleen of tumor bearing mice increased significantly as compared to non-tumor bearing mice particularly at early time points after tumor initiation.

In a similar experiment, an antibody targeting CD22, which preferentially depletes B10 cells (IgG2c), was purified and was given to mice intraperitoneally (i.p.) (100 µg/mouse in 200 µl of PBS) on days −7, 0 and 7 (300 µg/mouse total) to deplete B10 cells ("test group"). A second group of mice received a pan-B cell-depleting antibody (IgG2c, 250 µg/mouse) via the same mode of administration, that was only given at day −7 due to its durable depletion of mature B cells ("B cell control group"), as compared to the antibody preferentially depleting B10 cells. As controls, parallel groups of mice ("isotype control group") were given isotype-matched control monoclonal antibody, in the same dosage amount, mode of administration, and frequency as compared to the treatment antibodies. Tumor volumes were monitored and calculated using the following equation: $V=(L \times W \times W)/2$, where V=volume (cm$^3$), L=length, and W=width (cm). Tumor size was monitored for up to 30 days after the tumor injection, with mice euthanized before tumor volumes exceeded 2.0 cm$^3$. Mean tumor volumes were calculated and are shown for as long as each group of mice retained more than half of the original number of mice. Kaplan-Meier plots were used to show mouse survival.

Figure 3:
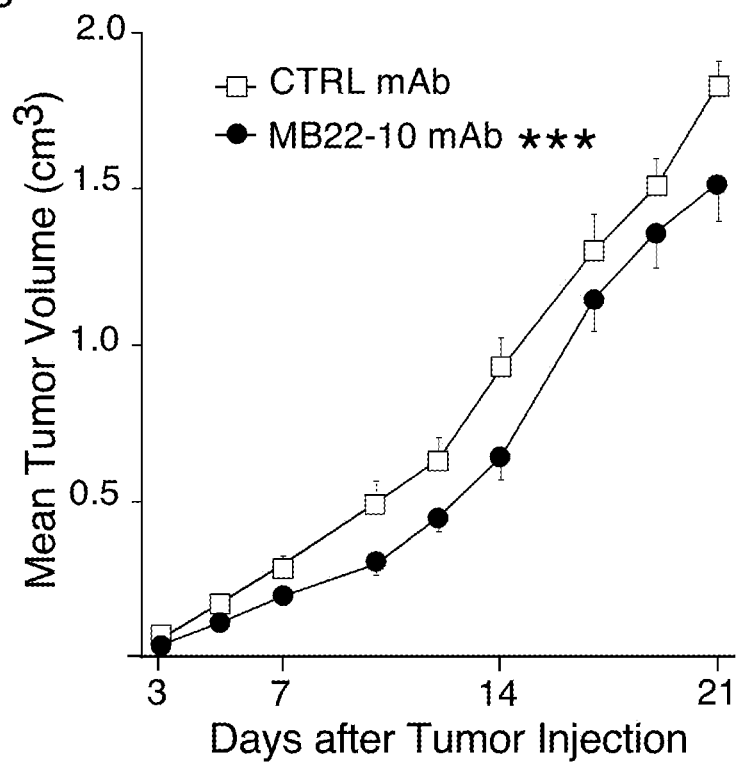
FIG. 3 is a graph showing B10 cell depletion inhibits MC38 tumor growth. Mice were given MB22-10 mAb to deplete B10 cells or control mAb on days −7, 0, and 7 before they were given either PBS or MC38 cells ($2\times10^6$) on day 0. Values represent mean (±SEM) tumor volumes pooled from 6 independent experiments (n=23 mice per group). Significant differences between groups are indicated: ***, p<0.001.
Figure 4:
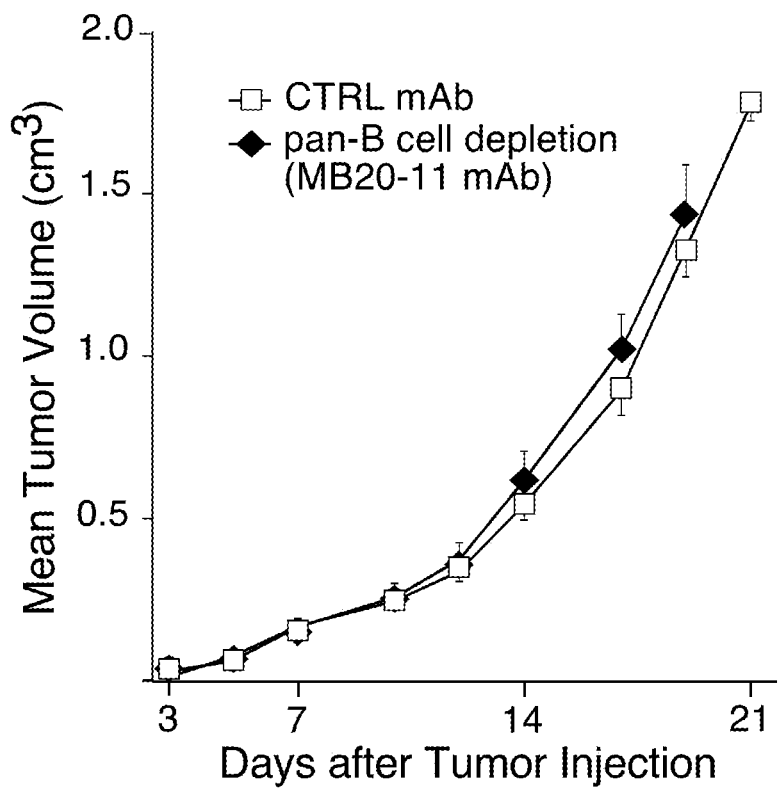
FIG. 4 is a graph showing that total B cell depletion does not alter MC38 tumor growth. Mice were given either CD20 (MB20-11) mAb to deplete all mature B cells or an isotype-matched control (CTRL) mAb 7 days before they were given subcutaneous PBS or MC38 tumor cells ($2\times10^6$) on day 0. Mean (±SEM) tumor volumes for the indicated days were pooled from 2 independent experiments (n=8-10 mice per group). Differences between groups were not statistically significant.

B10 cell depletion significantly inhibited tumor growth relative to control monoclonal antibody treated mice, with average tumor volumes reduced by 37% ($P \leq 0.05$) at each time point in mice depleted of B10 cells as a result of treatment with an antibody preferentially depleting B10 cells (FIG. 3). There was no significant effect on tumor growth observed as a result of total B cell depletion relative to the control monoclonal antibody treated group (FIG. 4). Thus, a composition comprising an antibody that preferentially depletes B10 cells, administered in a method of treatment, had a significant therapeutic effect on tumor growth as a monotherapy even though a relatively high tumor dose of an aggressive tumor line was studied. This is the first demonstration to our knowledge of a CD22 antibody administration resulting in reduced growth of a solid non-lymphoid tumor.

Example 3

In this Example, a standard animal model and methods were used for (a) treatment of cancer or for promoting an anti-tumor immune responses; (b) immunotherapy which results in T cell activation or reactivation of a pre-existing immune response in an individual in which such pre-existing immune response is inhibited or suppressed; (c) assessing the initiation or enhancement of the effectiveness (e.g., therapeutic efficacy) of an immune checkpoint inhibitor; (d) assessing a reduction in toxicity of an immune checkpoint inhibitor, or enablement of therapeutic effects of the immune checkpoint inhibitor obtained with a lower dose. The methods comprise administering, in a combination therapy regimen, a combination comprising an antibody preferentially depleting B10 cells and one or more immune checkpoint inhibitors in mice with established tumors. In contrast with the model using MC38 tumors as described above in Example 2, established tumor volumes were 40-100 mm$^3$ in individual mice when treatment was started (day 0). An antibody for preferentially depleting B10 cells (MB22-10 monoclonal antibody, IgG2c, 100 µg/mouse) was given on days 0, 6 and 12 (300 µg/mouse total). Anti-PD-1 antibody (monoclonal antibody, 100 µg/mouse) was given on days 0, 3, 6 and 9 (400 µg/mouse total). Anti-CTLA-4 antibody (monoclonal antibody, 100 µg/mouse) was given on days 0, followed by treatments on days 3 and 6 (200 µg/mouse total). Different groups of mice received either monotherapy with an antibody preferentially depleting B10 cells or an immune checkpoint inhibitor, or two immune checkpoint inhibitors, or a combination comprising an antibody preferentially depleting B10 cells and an immune checkpoint inhibitor, or a combination comprising an antibody preferentially depleting B10 cells and more than one immune checkpoint inhibitor.

Figure 5:
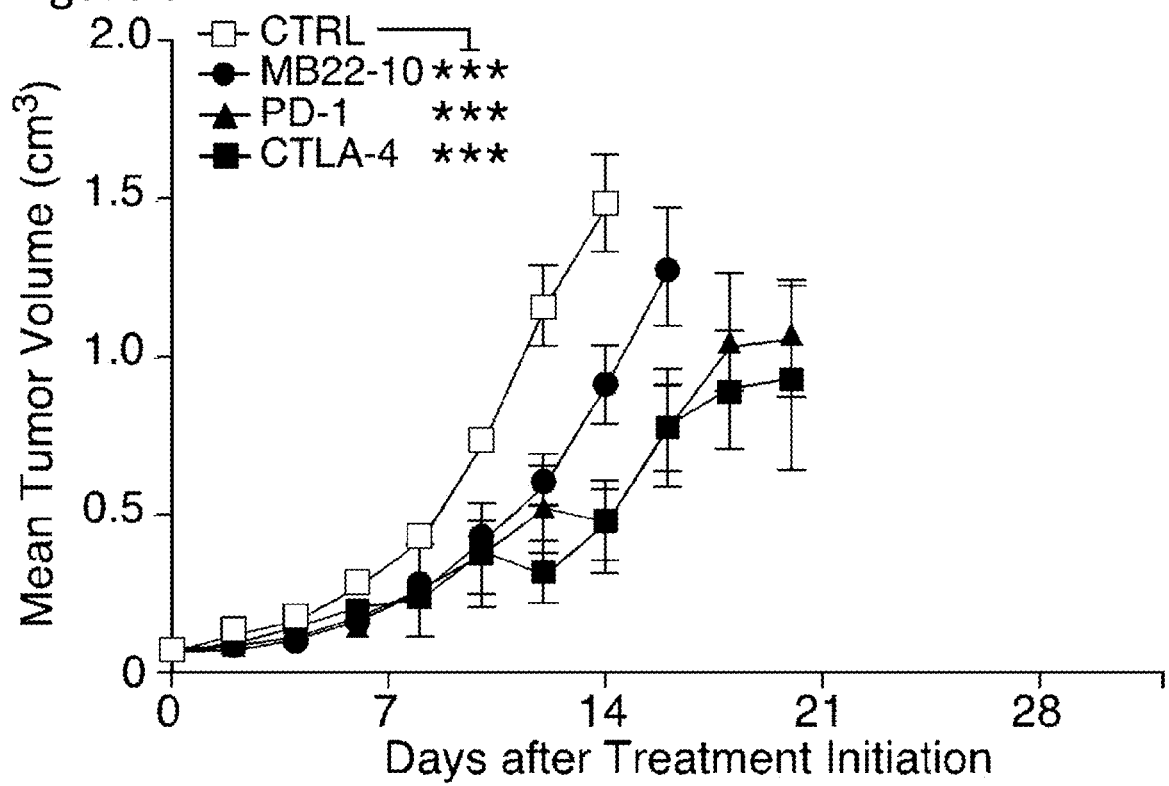
FIG. 5 is a graph showing therapeutic B10 cell depletion and immune checkpoint inhibitors delay tumor progression in mice with established MC38 tumors. Mice with MC38 tumor volumes of 40-100 mm$^3$ on day 0 were treated with MB22-10 or control (CTRL) mAb on days 0, 6, and 12, PD-1 mAb on days 0, 3, 6, and 9, or CTLA-4 mAb on days 0, 3, and 6. The graph shows mean (±SEM) tumor volumes starting after therapy initiation on day 0. Values represent pooled results from 2 independent experiments (n=9-10 mice per group). Significant differences between each of the indicated treatment groups and the control mAb-treated group are shown: ***, p<0.001.
Figure 6:
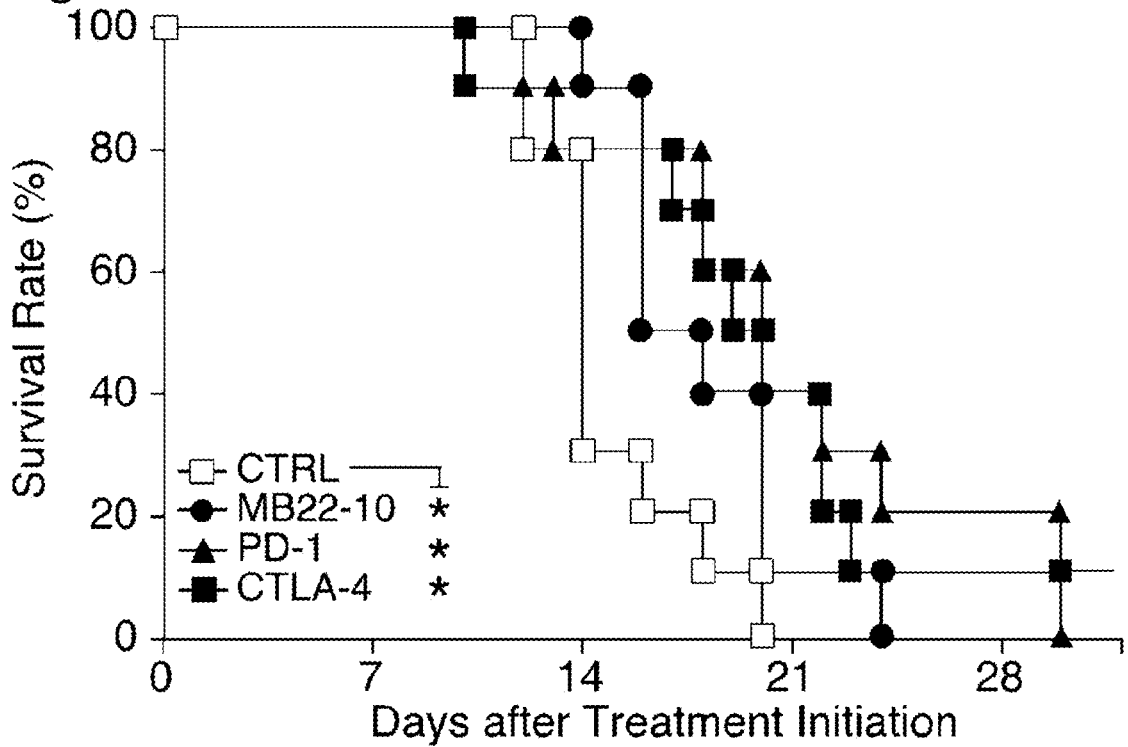
FIG. 6 is a graph showing therapeutic B10 cell depletion and immune checkpoint inhibitors prolong survival in mice with established MC38 tumors. Mice with MC38 tumor volumes of 40-100 mm$^3$ on day 0 were treated with MB22-10 or control (CTRL) mAb on days 0, 6, and 12, PD-1 mAb on days 0, 3, 6, and 9, or CTLA-4 mAb on days 0, 3, and 6. The graph shows Kaplan-Meier survival plots from FIG. 5 starting after therapy initiation on day 0. Values represent pooled results from 2 independent experiments (n=9-10 mice per group). Significant differences between each of the indicated treatment groups and the control mAb-treated group are shown: *, p<0.05.

As shown in FIG. 5, there was a significant effect on MC38 tumor growth in mice receiving the monotherapies as compared to those receiving isotype control antibody treatment. As shown in FIG. 6, survival rates were also prolonged significantly in mice receiving the monotherapies as compared to those receiving isotype control antibody treatment, but there were no significant differences between groups of mice given either antibody that preferentially depletes B10 cells, anti-PD-1 antibody or anti-CTLA-4 antibody.

Figure 7:
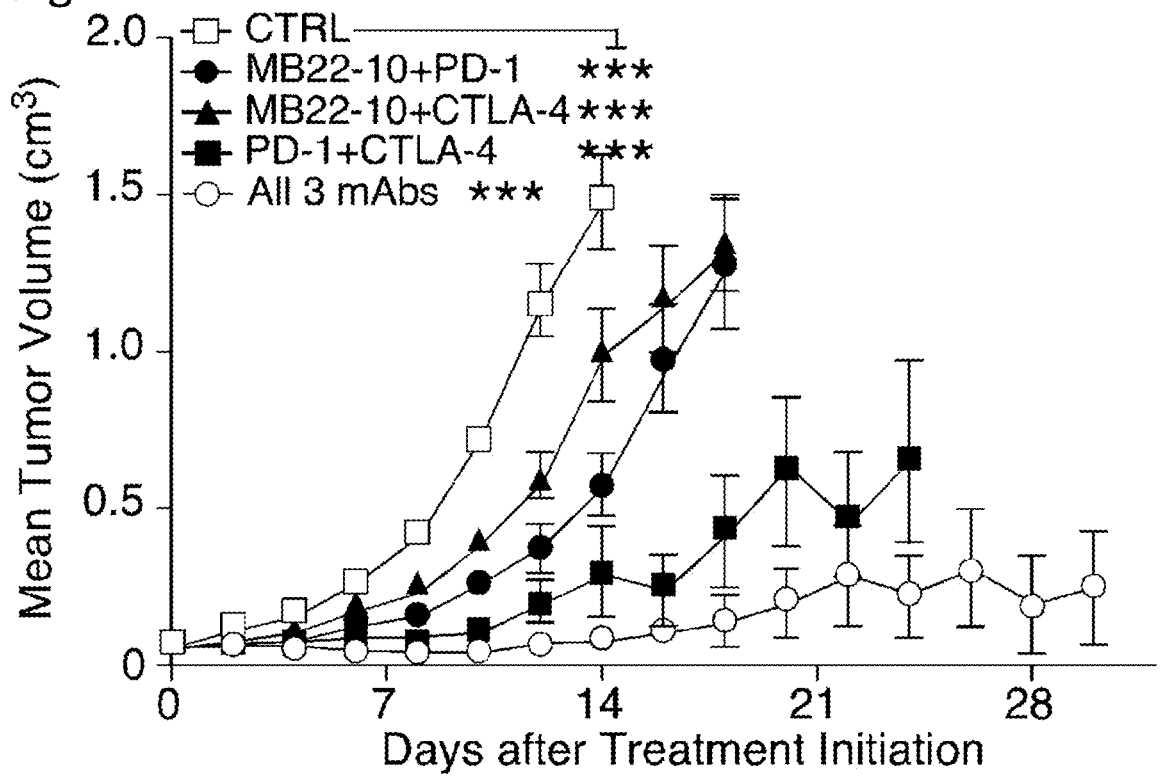
FIG. 7 is a graph showing therapeutic B10 cell depletion in mice with established MC38 tumors delays tumor progression and synergizes with immune checkpoint inhibitors to promote rejection. Mice with MC38 tumor volumes of 40-100 mm$^3$ on day 0 were treated with MB22-10 or control (CTRL) mAb on days 0, 6, and 12, PD-1 mAb on days 0, 3, 6, and 9, and/or CTLA-4 mAb on days 0, 3, and 6. The graph shows mean (±SEM) tumor volumes starting after therapy initiation on day 0. Values represent pooled results from 2 independent experiments (n=9-10 mice per group) carried out in parallel with FIG. 5 so the control treatment group is identical. Significant differences between each of the indicated treatment groups and the control mAb-treated group are shown: ***, p<0.001.
Figure 8:
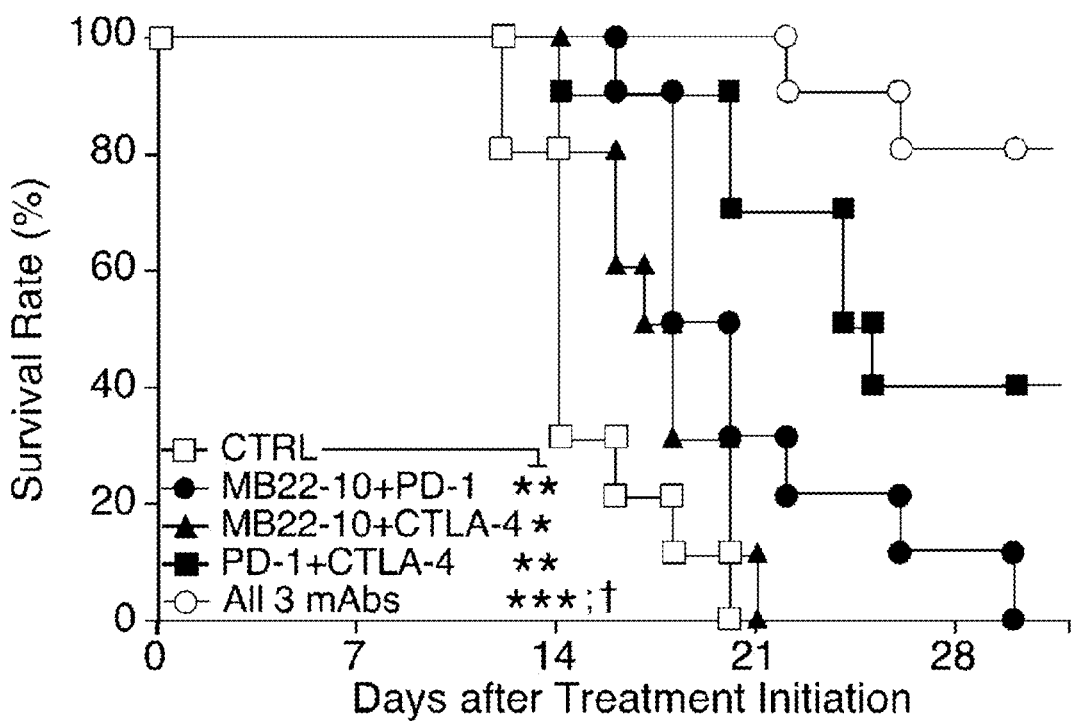
FIG. 8 is a graph showing therapeutic B10 cell depletion in mice with established MC38 tumors delays tumor progression and synergizes with immune checkpoint inhibitors to promote rejection. Mice with MC38 tumor volumes of 40-100 mm$^3$ on day 0 were treated with MB22-10 or control (CTRL) mAb on days 0, 6, and 12, PD-1 mAb on days 0, 3, 6, and 9, and/or CTLA-4 mAb on days 0, 3, and 6. Graphs show Kaplan-Meier survival plots starting after therapy initiation on day 0. Values represent pooled results from the 2 independent experiments (n=9-10 mice per group) shown in FIG. 7. Significant differences between each of the indicated treatment groups and the control mAb-treated group are shown: *, p<0.05, , p<0.01, *, p<0.001; and †, p<0.001 for the group of mice that received all three therapies versus the groups that received each combination of dual therapies.

As compared to mice receiving the isotype control antibody, mice treated with either (i) two immune checkpoint inhibitors, or (ii) a combination comprising an antibody preferentially depleting B10 cells and an immune checkpoint inhibitor, or (iii) a combination comprising an antibody preferentially depleting B10 cells and more than one immune checkpoint inhibitor showed significantly delayed mean tumor progression and reduced average tumor growth (FIG. 7). FIG. 8 shows that survival rates were also improved with the combination therapies when compared with the monotherapies. Most striking is the synergy observed in treatment with a combination comprising an antibody preferentially depleting B10 cells and more than one immune checkpoint inhibitor.

Figure 9:
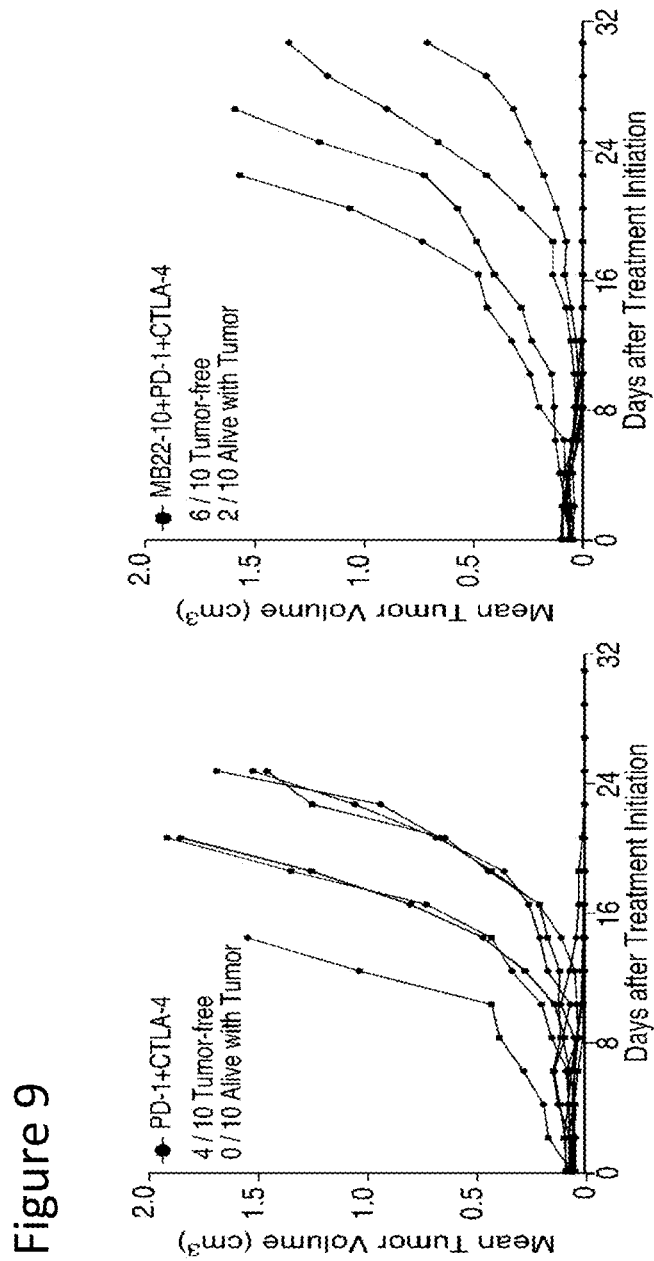
FIG. 9 is a set of graphs showing B10 cell depletion promotes tumor rejection in mice given PD-1 and CTLA-4 checkpoint inhibitors. Each line represents tumor volumes in individual mice given PD-1 and CTLA-4 mAbs (left panel) or MB22-10, PD-1, and CTLA-4 mAbs (right panel) as shown in FIG. 8, with the tumor status and survival of individual mice on day 31 provided.
Figure 10A:
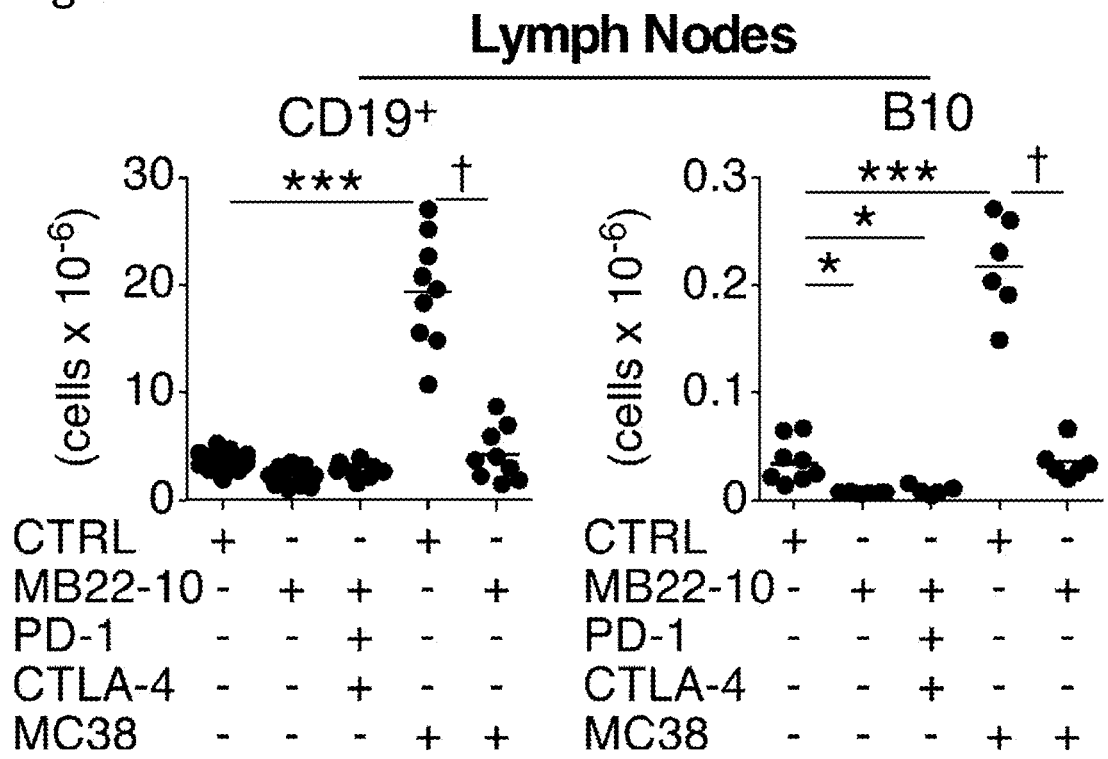
FIGS. 10A-10B are a set of graphs showing B10 cell depletion in mice with MC38 tumors. Mice were given either MB22-10 or control (CTRL) mAb on days 0, 7, and 14, PD-1 mAb on days 0, 3, 6, and 9, or CTLA-4 mAb on days 0, 3, and 6 as indicated. Some mice were also given subcutaneous MC38 tumor cells (2×10$^6$) on day 0 as indicated. CD19$^+$ B cell and B10 cell frequencies among single viable tumor-draining lymph node (FIG. 10A) and spleen (FIG. 10B) lymphocytes were assessed on day 21 by immunofluorescence staining with flow cytometry analysis. Numbers of total CD19$^+$ B cells and B10 cells within tumor-draining lymph nodes and spleen are shown for individual mice after treatment as indicated. Horizontal bars indicate mean cell numbers. All data were pooled from 2-4 experiments (n=6-22 total mice per group), with significant differences in means between the control and treatment groups indicated: , p<0.01; *, p<0.001; †, p<0.001.
Figure 10B:
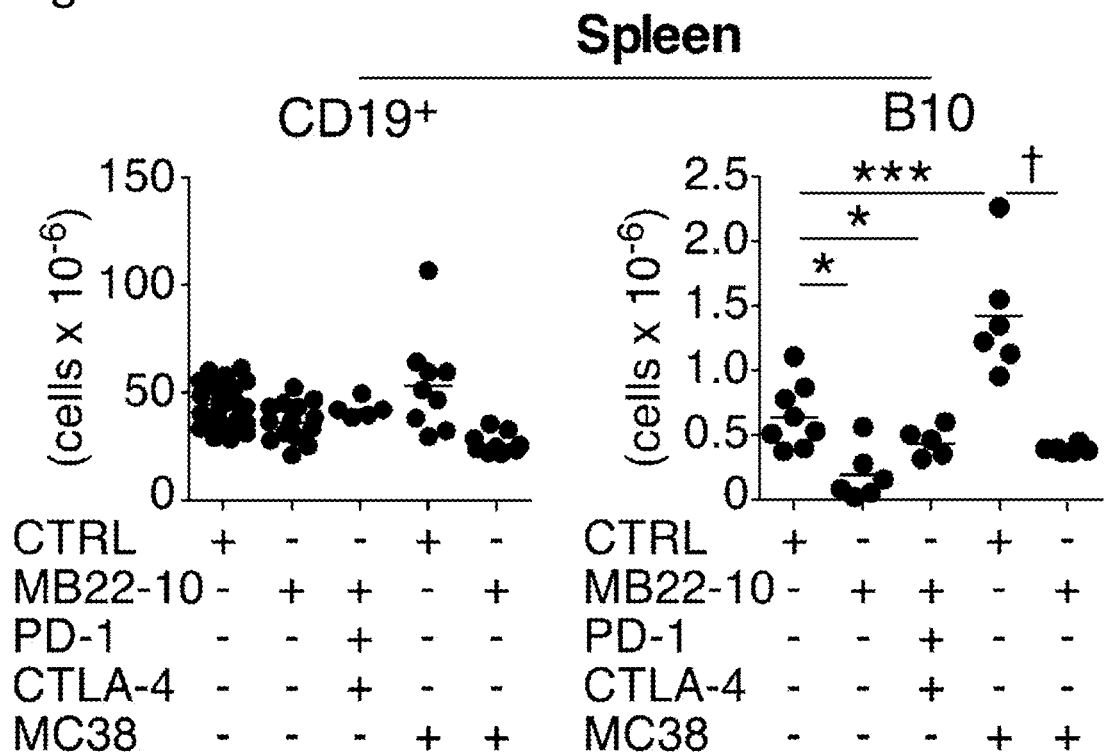

The results shown in FIG. 9 and demonstrate that tumor progression was slowest in mice treated with the three antibody combination where 6 of 10 mice rejected their tumors in comparison with 4 of 10 mice given the checkpoint inhibitor combination therapy. Thus, the triple antibody combination including B10 depletion and immune checkpoint inhibition resulted in slower tumor progression, more mice rejecting their tumors and increased overall survival.

The effects of combination therapies were next examined in mice without and with MC38 tumors to identify their synergistic effects on the immune system, particularly whether these antibody treatments were altering the total B cell numbers as measured by cells expressing CD19 and B10 cells in the draining lymph node and spleen of the treated mice. Mice were given either MB22-10 or control (CTRL) mAb on days 0, 7, and 14, PD-1 mAb on days 0, 3, 6, and 9, or CTLA-4 mAb on days 0, 3, and 6 as indicated and in the same dosages as above. Some mice were also given subcutaneous MC38 tumor cells ($2 \times 10^6$) on day 0 as indicated. $CD19^+$ B cell and B10 cell frequencies among single viable tumor-draining lymph node (FIG. 10A) and spleen (FIG. 10B) lymphocytes were assessed on day 21 by immunofluorescence staining with flow cytometry analysis. Numbers of total $CD19^+$ B cells and B10 cells within tumor-draining lymph nodes and spleen are shown for individual mice after treatment as indicated. Horizontal bars indicate mean cell numbers and asterisks indicate statistical significance. The antibody treatments did not change total $CD19^+$ B cell numbers in either the spleen or draining lymph node in the absence of tumor. Tumor-draining lymph node cellularity increased significantly in tumor bearing mice, but this was reversed in mice also treated with the B10 cell depleting antibody.

Treatment of normal non-tumor bearing mice with the B10 cell depleting antibody alone or in combination with immune checkpoint inhibitors reduced the number of B10 cells in both the lymph node and the spleen. Tumor bearing mice showed a significant increase in the number of B10 cells in both the lymph node and the spleen relative to mice without tumors, but and this increase was completely reversed in mice treated with a B10 cell depleting CD22 targeting antibody. Thus demonstrating that the B10 cell depleting mAb as a monotherapy is effective in depleting B10 cells the presence of tumor, with a resulting therapeutic benefit as demonstrated by reduced lymphadenopathy.

Example 4

Figure 11A:
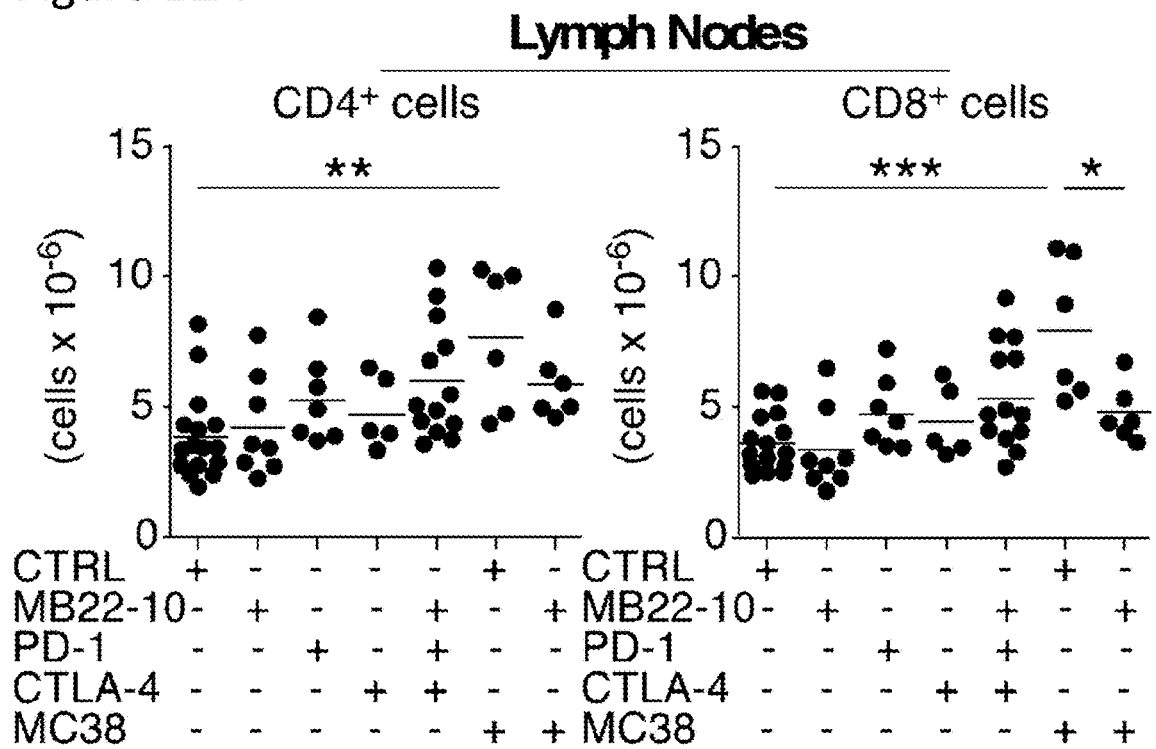
FIGS. 11A-11B are a set of graphs showing B10 cell depletion augments immune checkpoint inhibitor-driven T cell activation. Mice were given either MB22-10 or control (CTRL) mAb on days 0, 6, and 12, PD-1 mAb on days 0, 3, 6, and 9, and/or CTLA-4 mAb on days 0, 3, and 6. The indicated mice were also given subcutaneous MC38 tumor cells (2×10$^6$) on day 0. Viable single lymph node (FIG. 11A) and spleen (FIG. 11B) lymphocytes were examined on day 19 by immunofluorescence staining with flow cytometry analysis. CD4+ and CD8$^+$ T cell numbers in the lymph nodes and spleen are shown for individual mice after mAb treatments with or without MC38 tumors as indicated. Horizontal bars indicate mean cell numbers. All data were pooled from 2-5 independent experiments (n=6-16 total mice per group). Significant differences between control and treatment groups are indicated: *, p<0.05; , p<0.01; *, p<0.001.
Figure 11B:
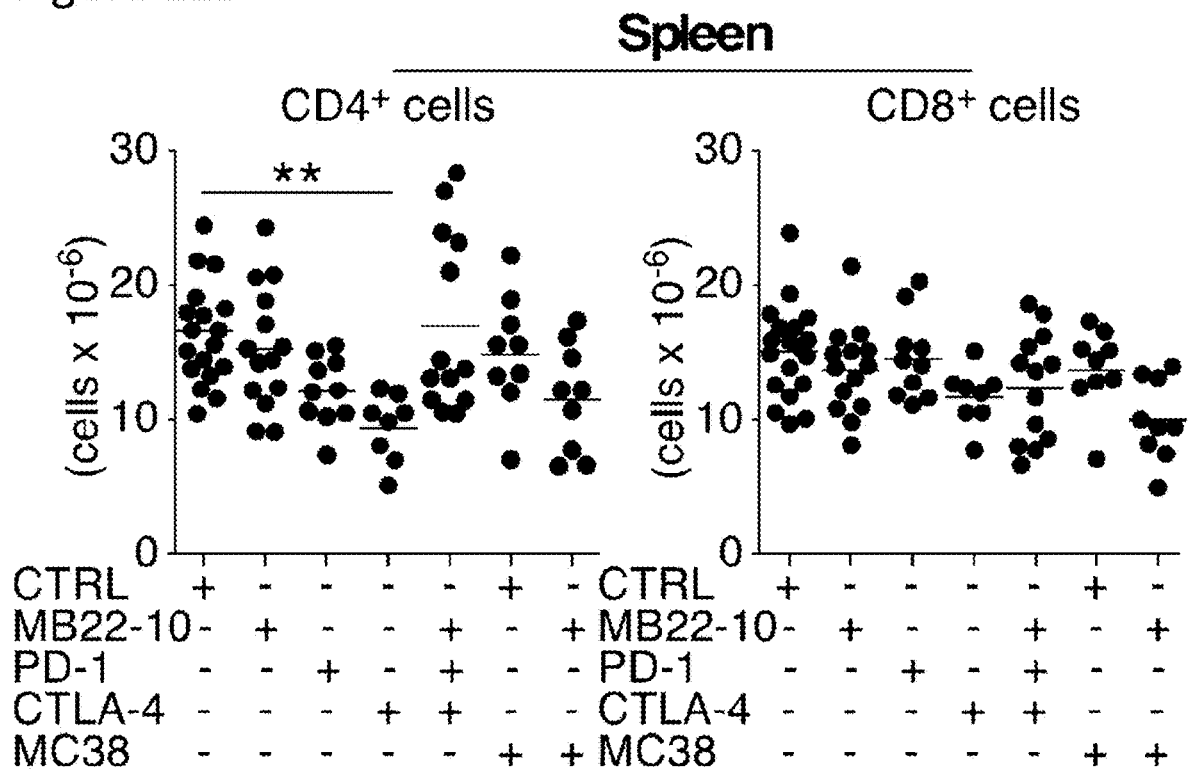

In this Example, shown in a standard animal model is treatment with an antibody preferentially depleting B10 cells by itself (monotherapy) or in a combination therapy regimen with an immune checkpoint inhibitor, that can augment (enhance, initiate and/or prolong) both $CD4^+$ and $CD8^+$ T cell activation, such cell activation playing an important role in mounting an antitumor immune response. Spleen and lymph node $CD4^+$ and $CD8^+$ T cell total numbers and activation were quantified on day 7 following one treatment by their patterns of cell surface CD44 and CD62L expression. As shown in FIG. 11A for mice without tumors, the relative number of lymph node $CD4^+$ cells and $CD8^+$ cells did not dramatically change in mice treated with either monotherapy or combination therapy as compared to mice receiving control antibody alone. As shown in FIG. 11B, the relative number of spleen $CD4^+$ cells and $CD8^+$ cells was reduced in mice treated with either anti-PD-1 or anti-CTLA-4 monotherapy but not as much in mice treated with a combination therapy of antibody that preferentially depleted B10 cells, anti-PD-1 antibody and anti-CTLA-4 antibody as compared to mice receiving control antibody. However, both $CD4^+$ cells and $CD8^+$ cells were increased within the tumor-draining lymph nodes of mice given MC38 tumors, and as shown in FIG. 11A.

Figure 12A:
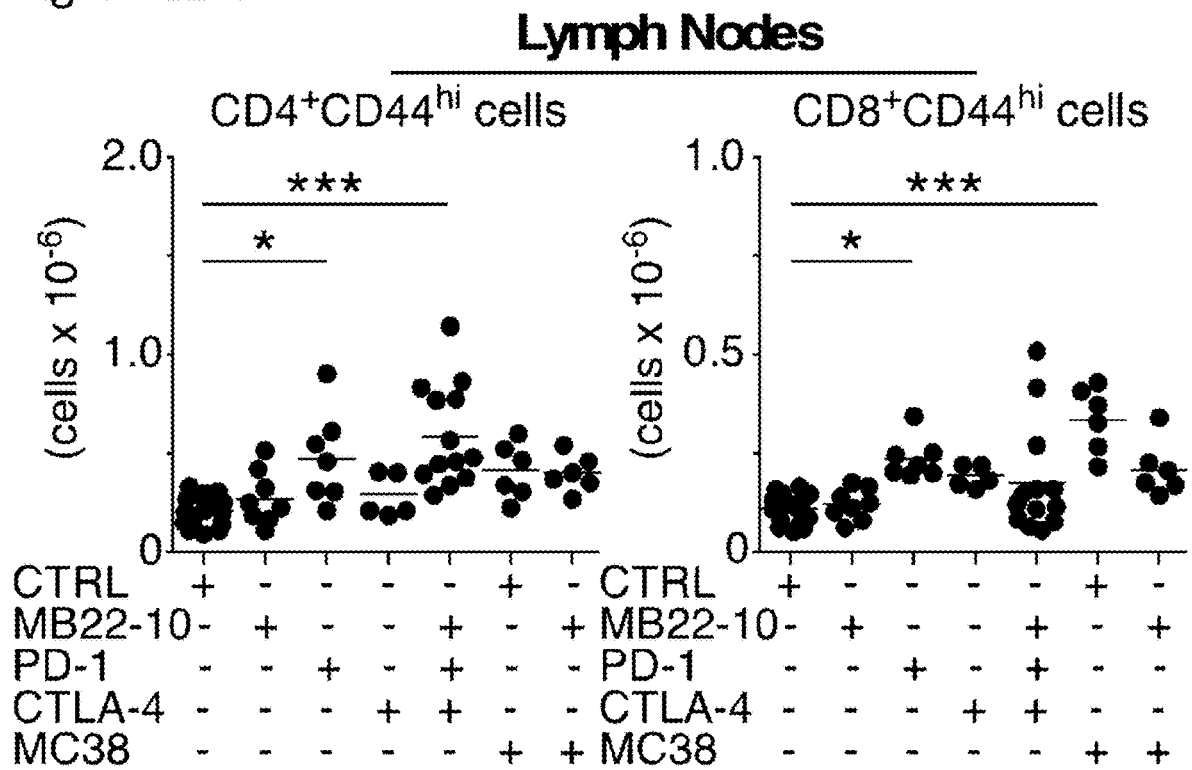
FIGS. 12A-12B are a set graphs showing B10 cell depletion augments immune checkpoint inhibitor-driven T cell activation. Mice were given either MB22-10 or control (CTRL) mAb on days 0, 6, and 12, PD-1 mAb on days 0, 3, 6, and 9, and/or CTLA-4 mAb on days 0, 3, and 6. The indicated mice were also given subcutaneous MC38 tumor cells (2×10$^6$) on day 0. Viable single lymph node (FIG. 12A) and spleen (FIG. 12B) lymphocytes from the mice shown in FIG. 11 were examined on day 19 by immunofluorescence staining with activated CD44$^{hi}$CD62L$^{lo}$ CD4$^+$ and CD8$^+$ T cell numbers in the lymph nodes and spleen shown for individual mice after mAb treatments with or without MC38 tumors as indicated. Horizontal bars indicate mean cell numbers. All data were pooled from 2-5 independent experiments (n=6-16 total mice per group). Significant differences between control and treatment groups are indicated: *, p<0.05; , p<0.01; *, p<0.001.
Figure 12B:
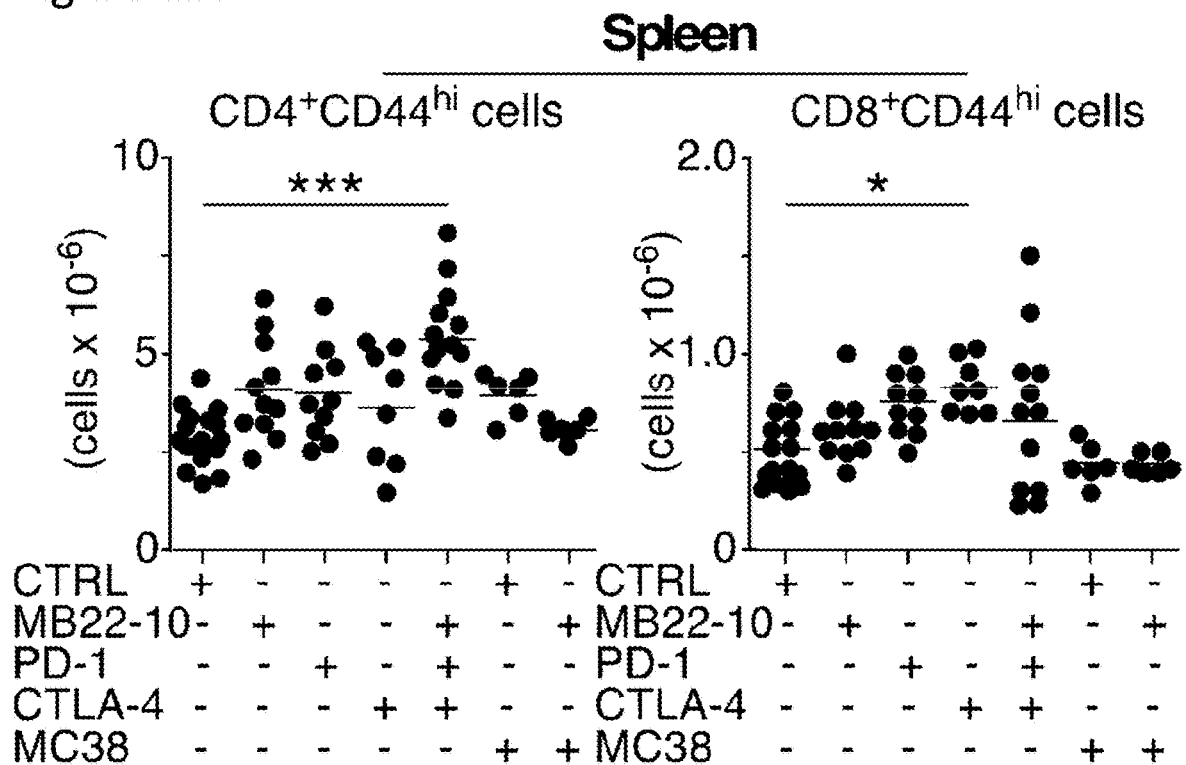

The number of activated $CD4^+$ T cells and of activated $CD8^+$ T cells in the spleen, which have low CD62L expression and high CD44 expression ($CD62L^{lo}CD44^{hi}CD4^+$, $CD62L^{lo}CD44^{hi}CD8^+$, respectively) was significantly increased by each monotherapy in mice without tumors; however, the most significant increase observed in the number of activated $CD4^+$ T cells and of activated $CD8^+$ T cells was following combination therapy comprising an antibody that preferentially depletes B10 cells and more than one immune checkpoint inhibitor, as compared to the other treatments (FIG. 12B). Lymph node $CD62L^{lo}CD4^+$ T cell numbers and $CD62L^{lo}CD8^+$ T cell numbers were also increased following combination therapy comprising an antibody that preferentially depletes B10 cells and more than one immune checkpoint inhibitor, as compared to control treatment (FIG. 12A). These results show that treatment with an antibody preferentially depleting B10 cells can contribute by itself or in combination with immune checkpoint inhibitors to activate T cells ($CD4^+$ T cells and $CD8^+$ T cells) in mediating an anti-tumor immune response. Thus, a technical solution relating to one aspect of the invention is that because an antibody preferentially depleting B10 cells by itself can augment both CD4 and CD8 T cell activation, it can enhance the effectiveness of any immune checkpoint inhibitor that is also directed to promoting T cell activation.

Figure 13:
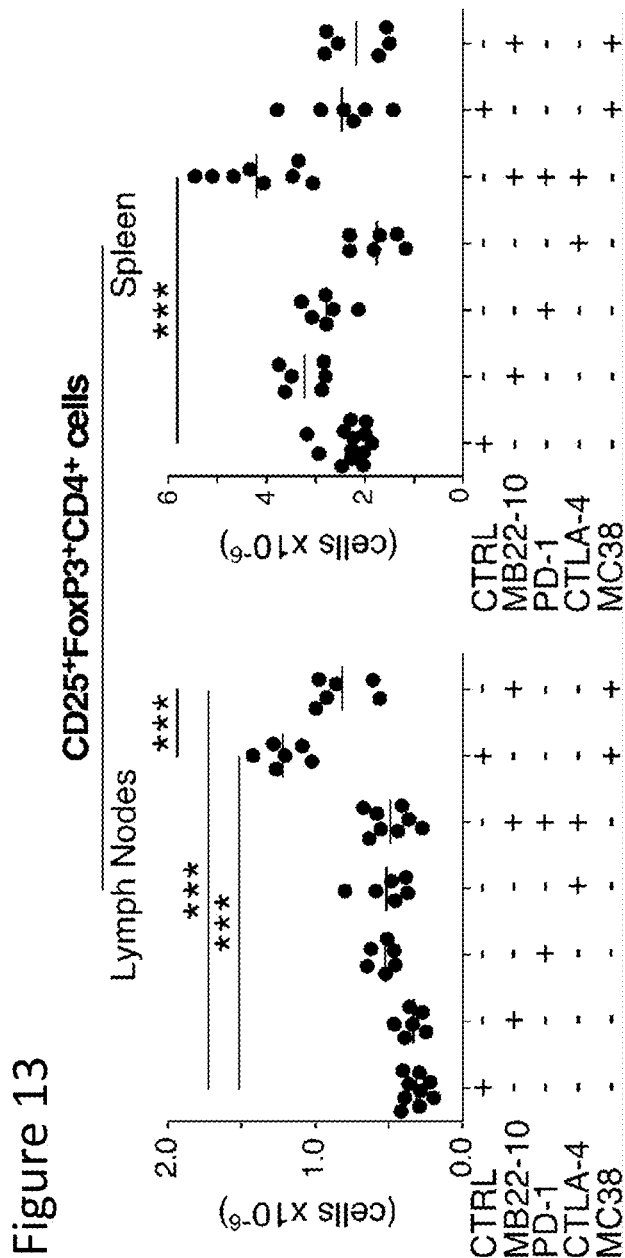
FIG. 13 is a set of graphs showing CD25$^+$FoxP3$^+$CD4$^+$ Treg cells in B10 cell depleted and checkpoint inhibitor treated and tumor-bearing mice. Mice were treated with MB22-10 or control (CTRL) mAb on days −7, 0, and 7, PD-1 mAb on days 1, 4, 7 and 10, and/or CTLA-4 mAb on days 1, 4, and 7. Some mice were given MC38 tumor cells (2×10$^6$) as indicated on day 0. Tumor-draining lymph node and spleen lymphocytes were then assessed on day 14 by immunofluorescence staining with flow cytometry analysis. Representative histograms show CD25$^+$FoxP3$^+$CD4$^+$ Treg cell frequencies of individual mice within the indicated gates. Numbers are the group means (±SEM) for lymph nodes and spleens of control (left panels) and MC38 tumor-bearing mice (right panels). Dot plots show cell numbers, with horizontal bars indicating group means. Data were pooled from 2-3 experiments (n=6-12 total mice per group).

The number of regulatory T cells (CD25+FoxP3+CD4+ cells) was also assessed in mice treated as described above. As shown in FIG. 13, monotherapy with any of the antibodies had no effect on the number of regulatory T cells in the lymph node or spleen. In contrast, tumor bearing mice had significantly higher levels of regulatory T cells in the spleen after treatment with the triple antibody combination. Numbers of $CD4^+$ regulatory T cells in untreated tumor bearing mice was significantly increased in the lymph node, but changes were not observed in the spleen. The increase in regulatory T cells observed in draining lymph nodes was reversed when the tumor bearing mice were treated with the CD22 antibody capable of depleting B10 cells. These results suggest that administration of the CD22 antibody that depletes B10 cells may contribute to decreased regulatory T cell responses and increased T cell activation in treated animals and thereby support more effective anti-tumor immune responses.

Example 5

Figure 14A:
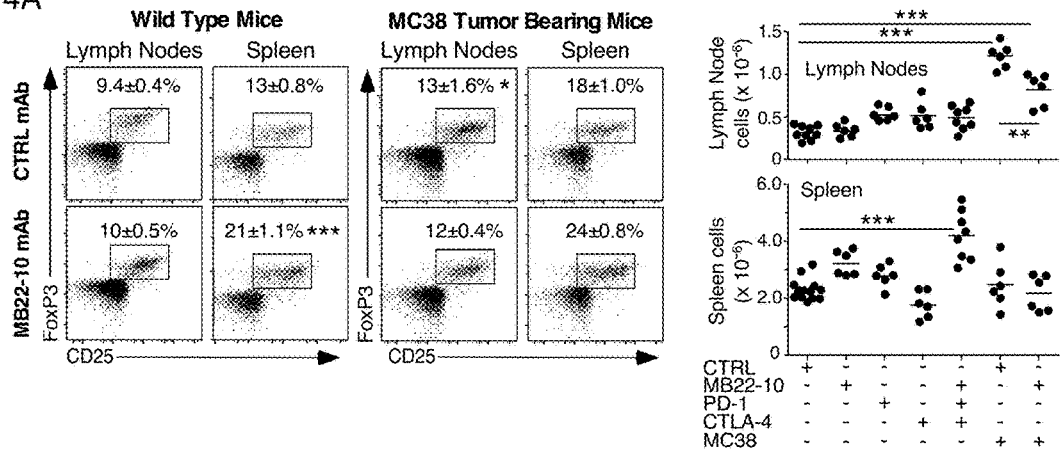
FIG. 14A-14C demonstrate B10 cell plus Treg cell depletion therapies, in conjunction with PD-1 mAb therapy, synergistically inhibit MC38 tumor growth.
Figure 14B:
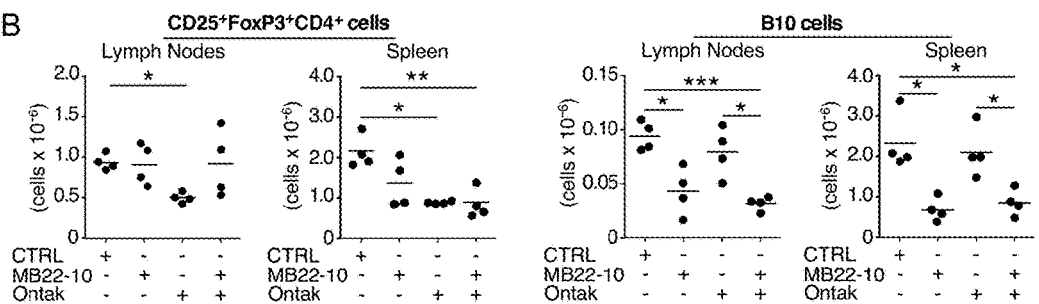
Figure 14C:
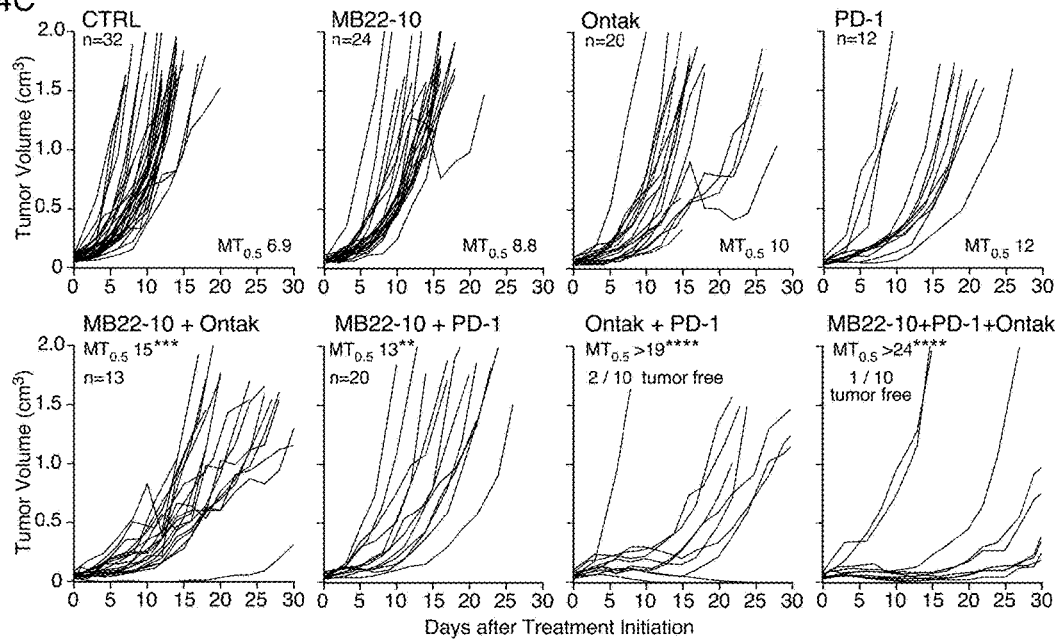

Using the standard animal models and methods described in Examples 2 and 3, this example further illustrates initiation or enhancement of an anti-tumor response in a treatment comprising an antibody preferentially depleting B10 cells and an immune checkpoint inhibitor. The immune checkpoint inhibitor used in these experiments was denileukin diftitox (Ontak). Mice with established MC38 tumors (40-100 mm$^3$) received either an antibody preferentially depleting B10 cells or isotype-matched control antibody treatment on days 0, 6, and 12 (300 µg/mouse total). Denileukin diftitox was administered on days 0, 3, and 6 (15 µg/mouse total) as a monotherapy to one group of mice, or in combination therapy with mice that received an antibody preferentially depleting B10 cells. As shown in FIG. 14C, there is a significant (p<0.05) reduction in tumor progression (mean tumor volume) in individual mice receiving combination therapy comprising an antibody preferentially depleting B10 cells and PD-1 and/or an IL-2-toxin fusion protein (denileukin diftitox) as compared to individual mice receiving monotherapy comprising an IL-2-toxin fusion protein (denileukin diftitox). Further, the combination of an antibody preferentially depleting B10 cells in combination with a PD-1 inhibitor and IL-2-toxin fusion protein (denileukin diftitox) synergistically inhibit tumor growth as demonstrated in FIG. 14C. Thus, a technical solution relating to one aspect of the invention is that an antibody preferentially depleting B10 cells can work in synergy with an immune checkpoint inhibitor in initiating, enhancing, or prolonging an anti-tumor response, as compared to monotherapy involving an immune checkpoint inhibitor.

Figure 15A:
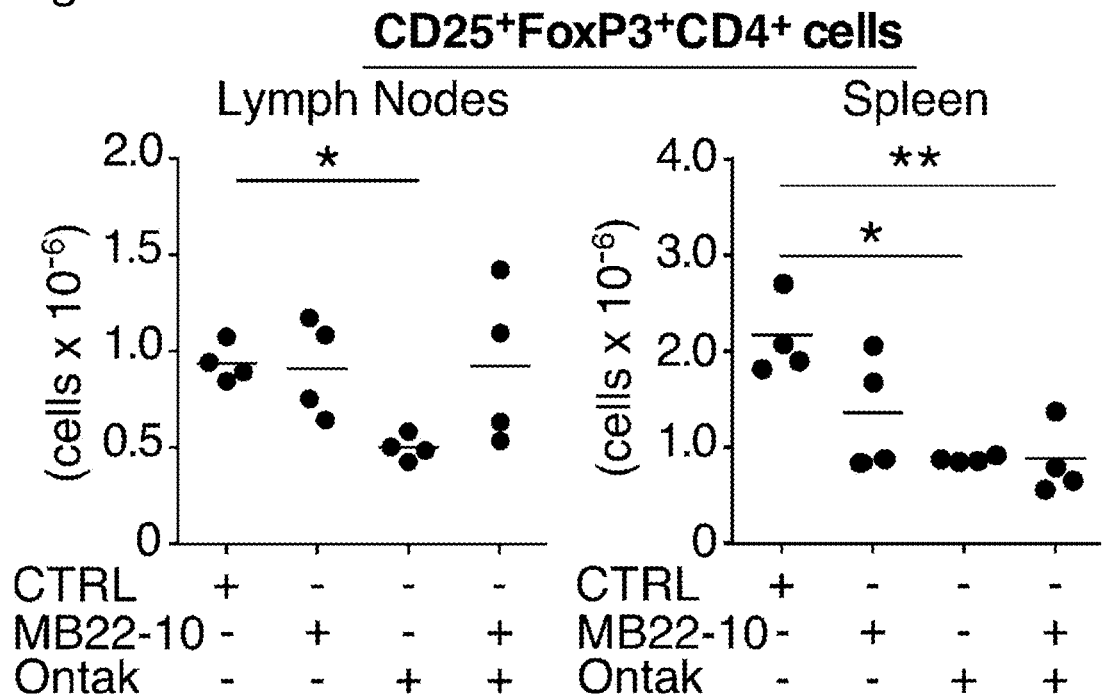
FIGS. 15A-15B are a set of graphs showing MB22-10 mAb and Ontak independently deplete B10 cells and Treg cells in mice with MC38 tumors, respectively.
Figure 15B:
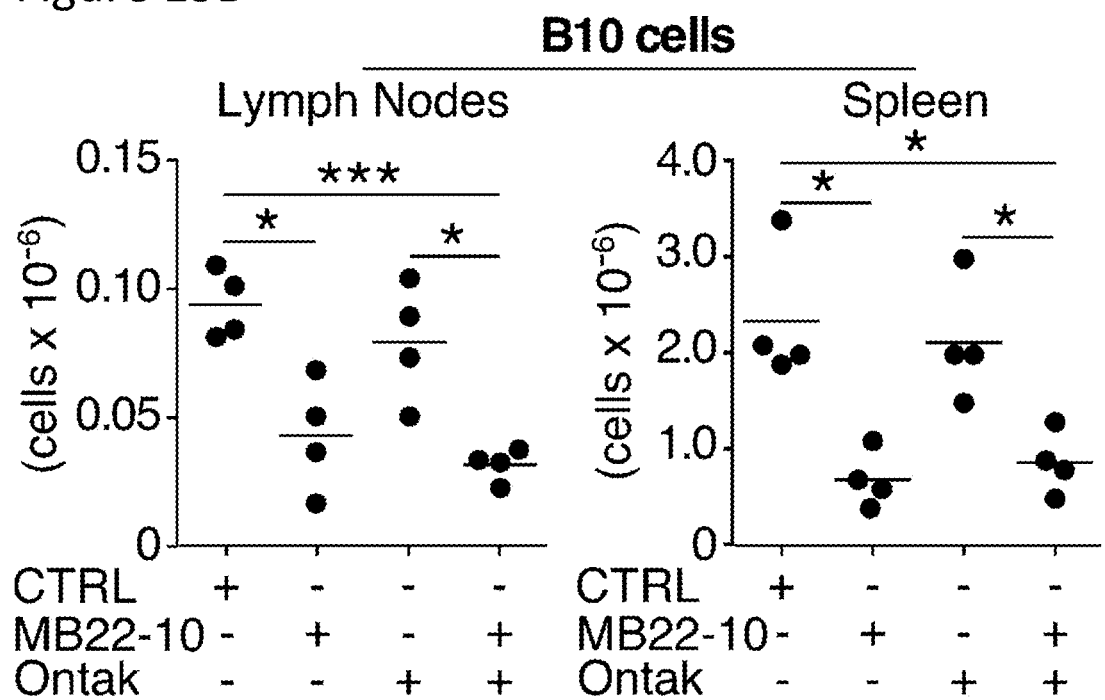

A similar experiment was carried out to assess the relative effect of the CD22 antibody and IL-2-toxin fusion protein (denileukin diftitox) to deplete B10 cells and regulatory T cells in mice. The experiment was performed as indicated above in mice with established MC38 tumors and the results are depicted in FIG. 15A (regulatory T cells) and FIG. 15B (B10 cells). The results are shown for the spleen and draining lymph nodes 9 days after treatment initiation with the CD22 antibody, the IL-2 toxin fusion protein or the combination. The numbers of B10 cells was only decreased in the spleen and lymph nodes of mice treated with the CD22 antibody either alone or in combination with the IL-2 toxin fusion protein. As shown in FIG. 15A the numbers of T regulatory cells were significantly reduced in the spleens of mice treated with the IL-2 toxin fusion protein alone or in combination with the CD22 antibody, but the regulatory T cells were only reduced significantly in lymph nodes of mice treated with the IL-2 fusion protein. The combination therapy did not result in a reduction in the number of regulatory T cells in the lymph node. These results suggest that administration of the CD22 antibody that depletes B10 cells may contribute to decreased regulatory T cell responses and increased T cell activation in treated animals and thereby support more effective anti-tumor immune responses.

Example 6

The CD22 antibody used in these preclinical experiments was specific for mouse CD22, but exhibits functional properties that are not shared by other anti-mouse CD22 mAbs. Specifically, most CD22 specific antibodies are not capable of depleting B10 cells in vivo. As discussed more fully above, the epitope through which the antibody binds in CD22 is likely to be distinct and their spatial interactions at the cell surface that induce homotypic adhesion and not ADCC or CDC are key features of a CD22 specific antibody for use in the methods provided here. We therefore sought to identify antibodies specific for human CD22 with the ability to mimic the mouse MB22-10 antibody in its capacity to preferentially deplete B10 cells. Fully-human, humanized, or chimerized monoclonal antibodies will be useful as human therapeutics in the methods provided herein.

The novel antibodies we selected from a large functional screen of well characterized CD22 antibodies are called HB22-103, HB22-106, HB22-107 and HB22-115. FIG. 22 provides a sequence alignment of the heavy and light chain variable regions of these antibodies with other human CD22 specific antibodies. The CDRs are highlighted (gray) for each of the chains and labeled. FIGS. 16-21 provide our initial characterization of the ability of these antibodies to preferentially deplete B10 cells.

Figure 16A:
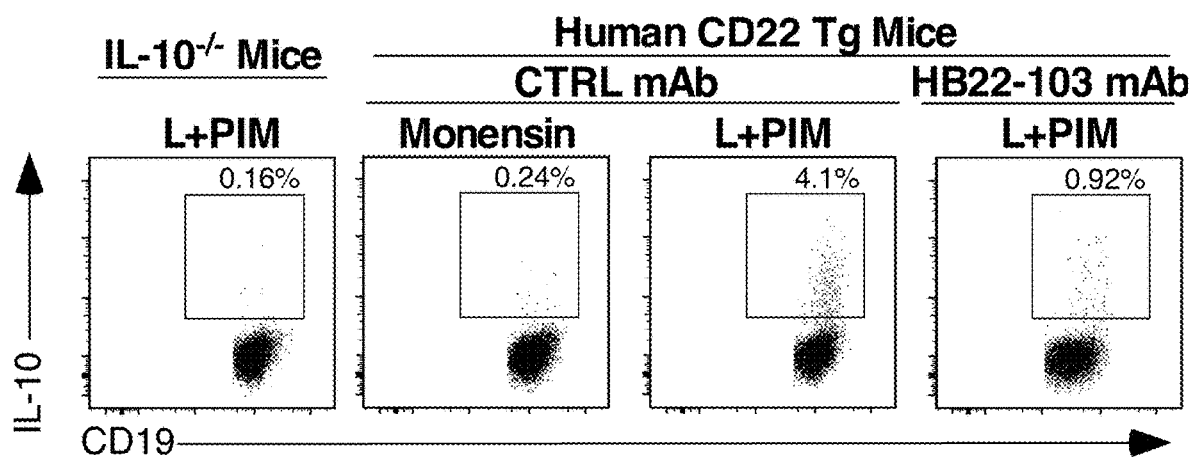
FIGS. 16A-16B are a set of FACScan scatter plots and a graph showing B10 cell depletion in transgenic mice expressing human CD22 using anti-human CD22 mAbs. Transgenic mice generated using the human CD22 gene with its endogenous regulatory elements expressed cell-surface human CD22 on B cells to the same extent as human blood B cells. These transgenic mice were crossed with mouse CD22$^{-/-}$ mice to generate hCD22-Tg$^{+/+}$mCD22$^{-/-}$ transgenic (hCD22-Tg) offspring. hCD22-Tg mice were given either HB22-103, HB22-107, HB22-115 or an isotype-matched (IgG1) mAb (250 µg/mouse) on day 0. IL-10 competent B10 cells within spleens were quantified 7 days later, with spleen lymphocytes from IL-10$^{-/-}$ mice assessed as a negative control. Purified lymphocytes were cultured with monensin alone or stimulated ex vivo with LPS, PMA, ionomycin, and monensin (L+PIM) for 5 h. All lymphocytes were stained for cell surface CD19 and intracellular IL-10 to quantify B10 cell frequencies.
Figure 16B:
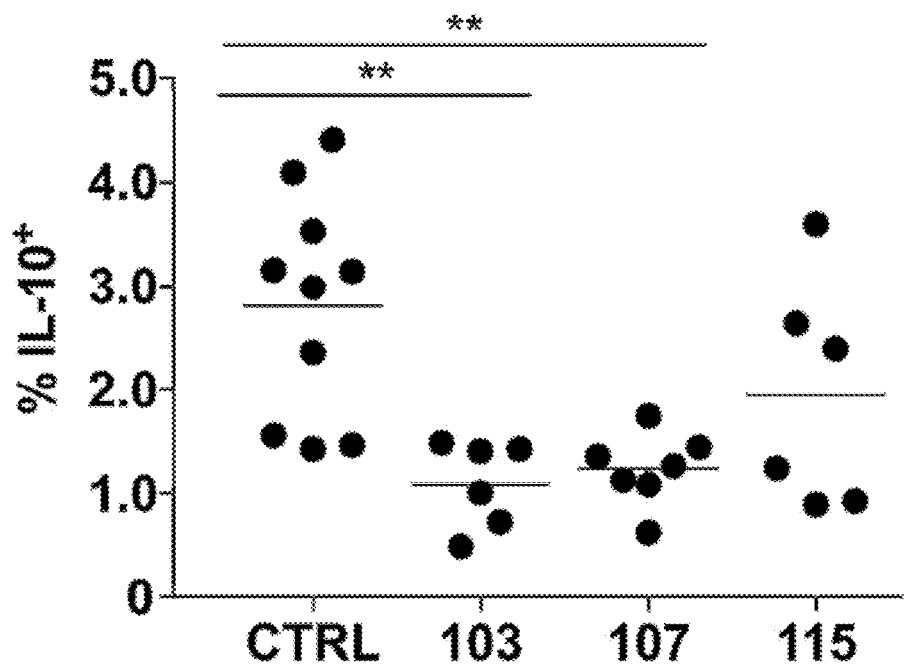
Figure 17A:
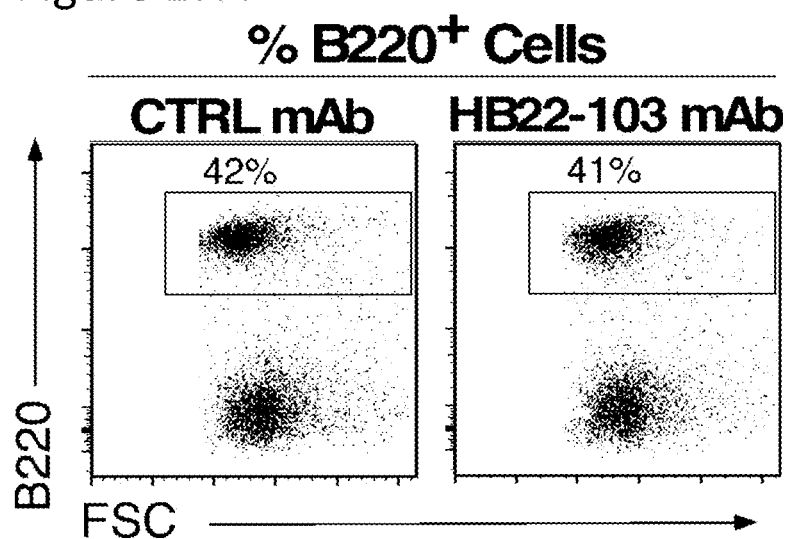
FIGS. 17A-17B show a set of FACScan scatter plots and a graph showing B10 cell-depleting mAbs in hCD22-Tg mice do not clear most spleen B cells. Spleen lymphocytes isolated from hCD22-Tg mice given either HB22-103, HB22-107, HB22-115 or an isotype-matched (IgG1) mAb (250 mg/mouse) 7 days earlier in FIG. 16 were assessed for B220$^+$ B cell (pan B cell) frequencies by immunofluorescence staining.
Figure 17B:
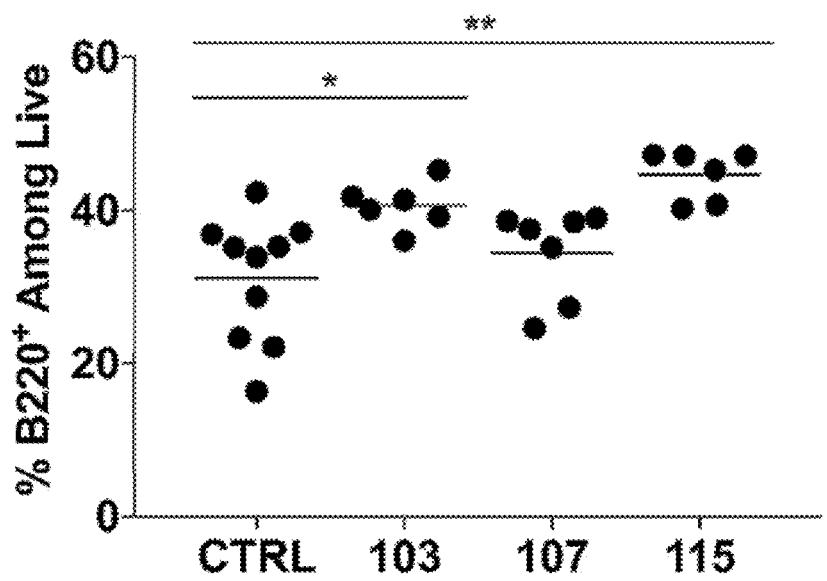
Figure 18A:
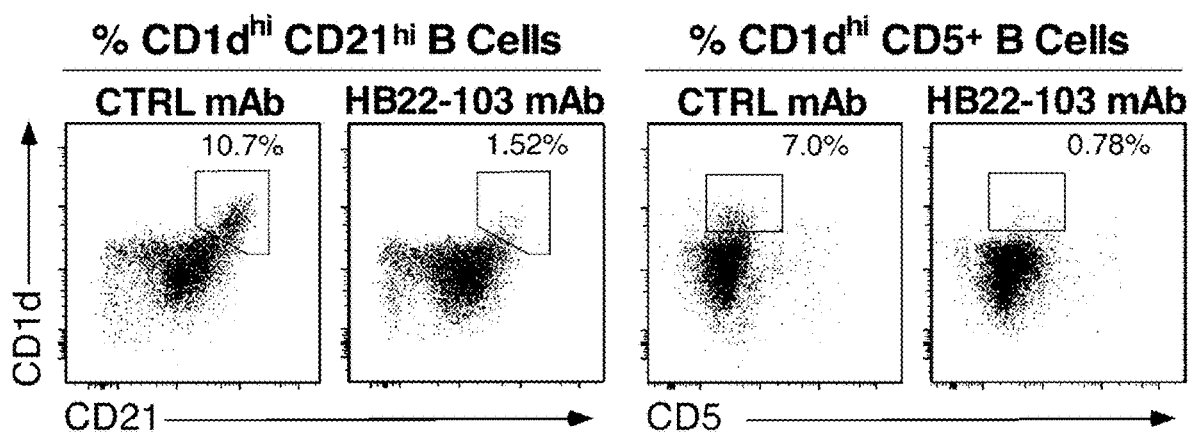
FIGS. 18A-18B show scatter plots and graphs showing B10 cell-depleting mAbs in hCD22-Tg mice clear most marginal zone (CD1d$^{hi}$CD21$^{hi}$) phenotype and CD1d$^{hi}$CD5$^+$ B cells from the spleen. Spleen lymphocytes isolated from hCD22-Tg mice given either HB22-103, HB22-107, HB22-115 or an isotype-matched (IgG1) mAb (250 µg/mouse) 7 days earlier in FIG. 16 were assessed for CD1d, CD21, CD5 and CD19 expression by immunofluorescence staining.
Figure 18B:
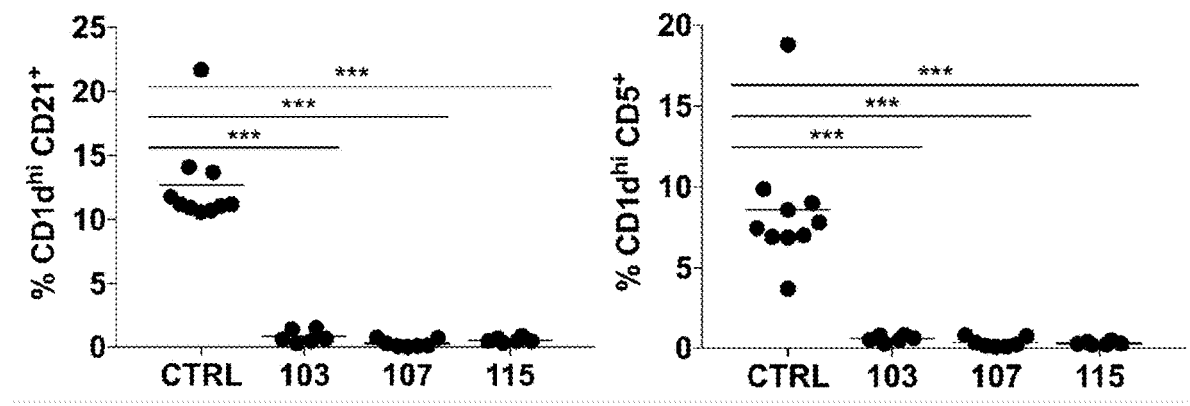

In their in vivo assessment, the ability of the monoclonal antibodies to deplete B10 cells in the spleen was evaluated by administering 250 µg of each of the indicated antibodies to human CD22 transgenic mice from a large functional screen of well characterized CD22 antibodies. Spleen mononuclear cells were collected 7 days after antibody administration and were stimulated in vitro with monensin, LPS, PMA and ionomycin for 5 hours and then selected using CD19 to identify B cells and cytoplasmic IL-10 expression to identify IL-10 competent B cells. The double positive cells represent the B10 cells. B10 cell numbers found in the transgenic mice following treatment (See FIG. 16A) in vivo with the HB22-103, HB22-106, HB22-107, HB22-115 antibodies were compared to the number in control treated mice as shown in FIG. 16B. The HB22-103 and HB22-107 CD22 antibodies were able to significantly deplete the number of IL-10 competent B10 cells in the spleen by 60-80% as occurs with the MB22-10 antibody in wild type mice (FIG. 16). Similarly, the HB22-103, HB22-107, and HB22-115 antibodies did not deplete the majority of spleen B cells (FIG. 17), but did effectively eliminate the CD1d$^{hi}$CD21$^{hi}$ and CD1d$^{hi}$CD5$^+$ cell subsets from the spleen (FIG. 18). As occurs with the MB22-10 antibody in mice, circulating B cell numbers decrease (FIG. 19) and the cell surface density of CD19 and CD22 on circulating B cells was downregulated after treatment with each of the CD22 antibodies (FIGS. 20-21). CD22 levels were down regulated on the remaining B cells in the antibody treated mice, but the cells were still capable of binding mIgG1 showing that the antibodies bind B cells in vivo. Thereby, the HB22-103, HB22-107, and HB22-115 exhibit many of the functional characteristics of the MB22-10 antibody and represent potential candidates for advancement to the clinic.

Figure 19A:
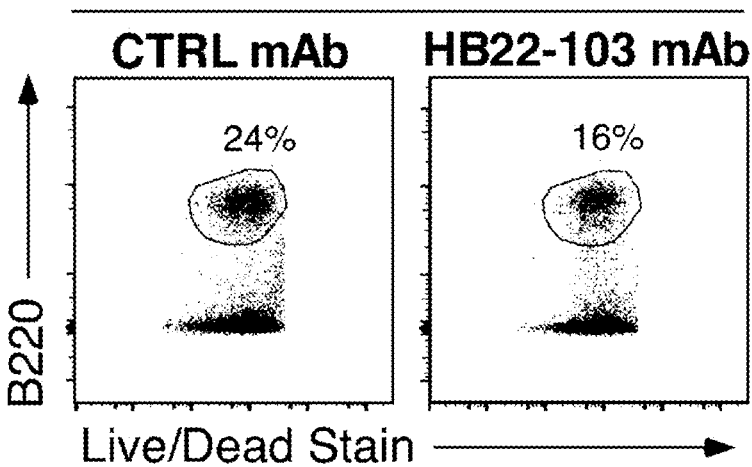
FIGS. 19A-19B show dot plots and scatter plots demonstrating B10 cell-depleting mAbs in hCD22-Tg mice reduce circulating B cell frequencies. Blood lymphocytes isolated from hCD22-Tg mice given either HB22-103, HB22-107, HB22-115 or an isotype-matched (IgG1) mAb (250 µg/mouse) 7 days earlier in FIG. 16 were assessed for relative B220$^+$ B cell frequencies by immunofluorescence staining.
Figure 19B:
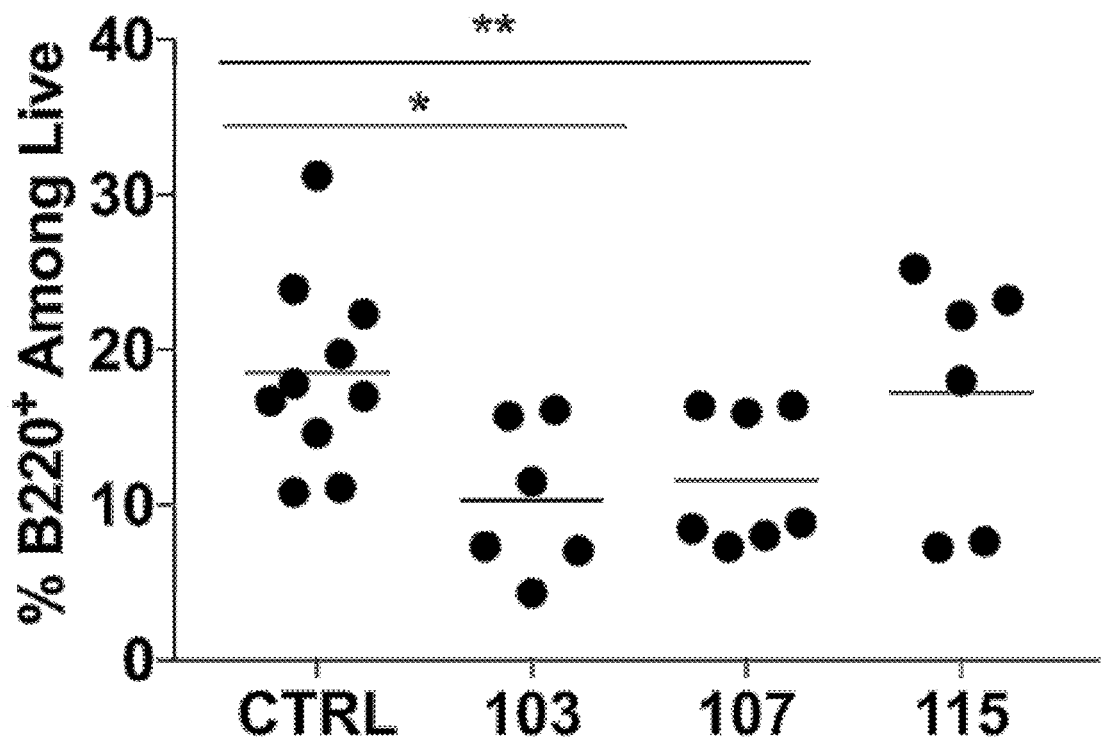
Figure 20A:
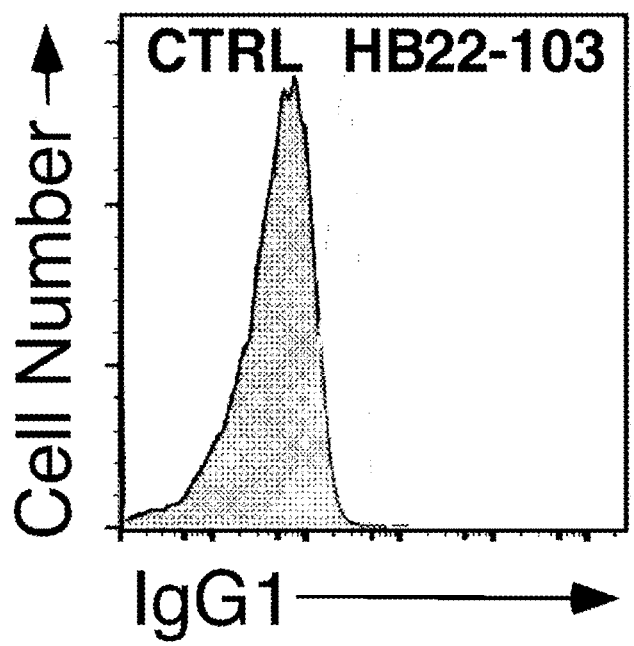
FIGS. 20A-20B are a set of histograms and scatter plots showing B10 cell-depleting mAbs in hCD22-Tg mice bind B220$^+$ B cells. Blood lymphocytes isolated from hCD22-Tg mice given either HB22-103, HB22-107, HB22-115 or an isotype-matched (IgG1) mAb (250 µg/mouse) 7 days earlier in FIG. 16 were assessed for relative HB22 mAb binding by immunofluorescence staining with fluorochrome-conjugated anti-mouse IgG1 isotype-specific antibody.
Figure 20B:
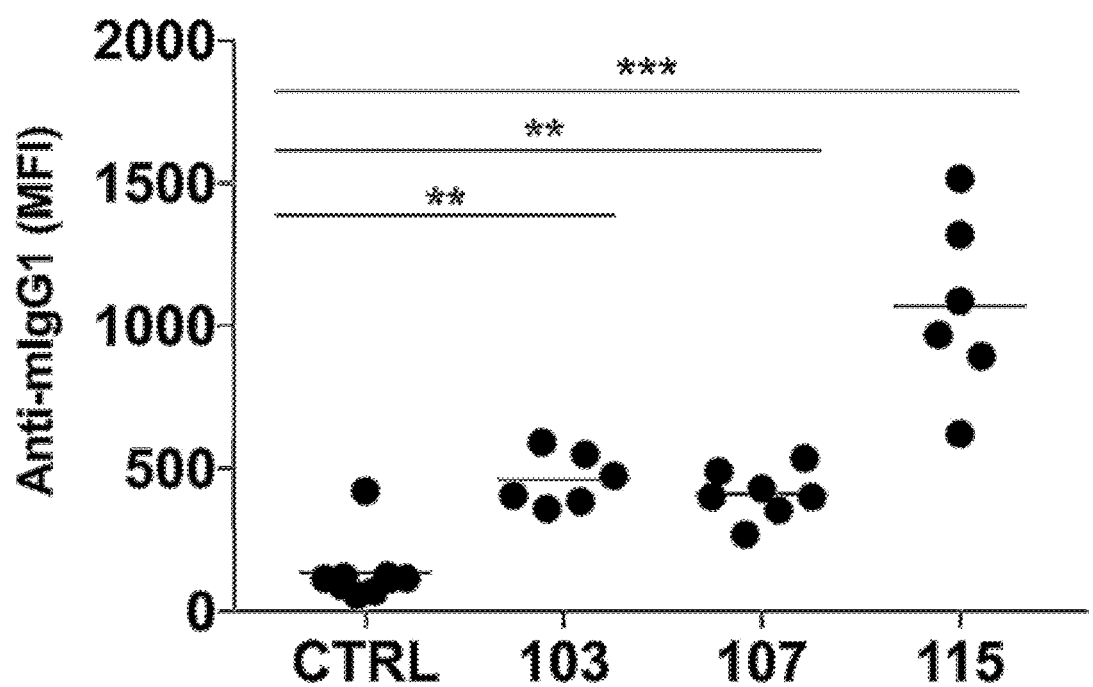
Figure 21A:
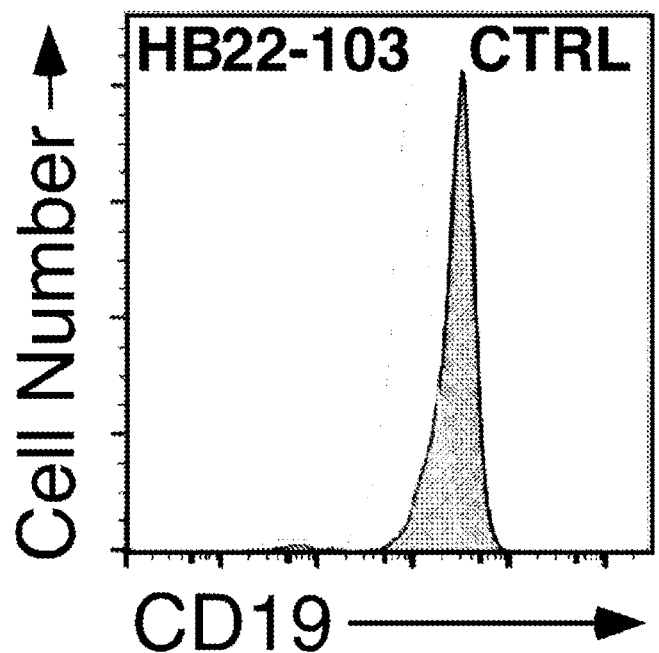
FIGS. 21A-21B are histograms and scatter plots showing B10 cell-depleting mAbs in hCD22-Tg mice reduce B cell surface CD19 expression. Blood lymphocytes isolated from hCD22-Tg mice given either HB22-103, HB22-107, HB22-115 or an isotype-matched (IgG1) mAb (250 μg/mouse) 7 days earlier in FIG. 16 were assessed for relative CD19 mAb binding by immunofluorescence staining.
Figure 21B:
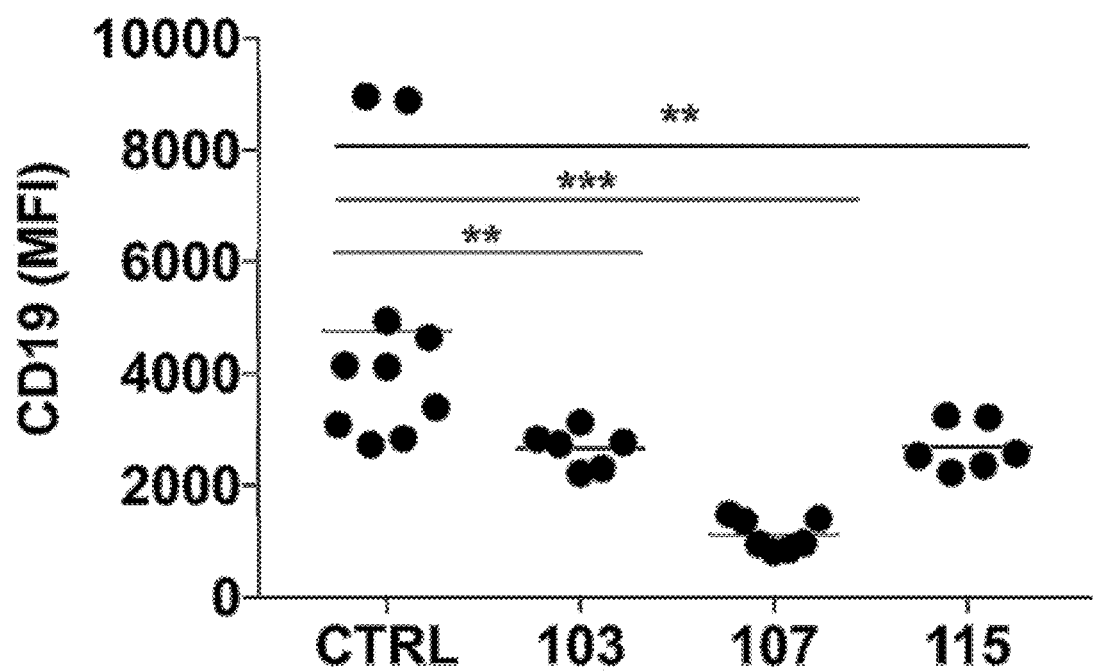

FIGS. 19-21 provide further characterization of three of the human CD22 specific antibodies. The mice were treated as described above with the indicated antibodies and the spleen was harvested 7 days after administration of the antibody. The total number of B220+ B cells in the spleen of mice treated each of the antibodies was significantly changed as compared to control treatment when HB22-103 or HB22-107 were administered to the mice as shown in FIGS. 19A and 19B. As shown in FIGS. 20A and 20 B, the percentage of cells expressing IgG1 was significantly increased in each of the CD22 antibody treated mice. As shown in FIGS. 21A and 21B the level of CD19 and the percentages of CD19+ cells were both significantly downregulated after treatment with each of the CD22 antibodies. Finally further treatment of the cells with a distinct CD22 antibody (HB22-7) demonstrated that the percentage of CD22 positive cells was significantly lower in cells from mice treated with the CD22 antibodies in vivo as compared to cells from control treated mice.

What is claimed is:

1. An antibody that specifically binds to human CD22 comprising a heavy chain variable region and a light chain variable region, the heavy chain variable region ("VH") comprising three complementarity determining regions (CDR): VH CDR1, VH CDR2, and VH CDR3, and the light chain variable region ("VL") comprising three complementarity determining regions: VL CDR1, VL CDR2, and VL CDR3, wherein:
   (a) the VH comprises CDR1 of SEQ ID NO: 27, CDR2 of SEQ ID NO: 29, and CDR3 of SEQ ID NO: 32 and the VL comprises CDR1 of SEQ ID NO: 40, CDR2 of SEQ ID NO: 41, and CDR3 of SEQ ID NO: 42;
   (b) the VH comprises CDR1 of SEQ ID NO: 27, CDR2 of SEQ ID NO: 30, and CDR3 of SEQ ID NO: 32 and the VL comprises CDR1 of SEQ ID NO: 37, CDR2 of SEQ ID NO: 38, and CDR3 of SEQ ID NO: 39;
   (c) the VH comprises CDR1 of SEQ ID NO: 28, CDR2 of SEQ ID NO: 31, and CDR3 of SEQ ID NO: 33 and the VL comprises CDR1 of SEQ ID NO: 34, CDR2 of SEQ ID NO: 35, and CDR3 of SEQ ID NO: 36; or
   (d) the VH comprising CDR1 of SEQ ID NO: 27, CDR2 of SEQ ID NO: 30, and CDR3 of SEQ ID NO: 32 and the VL comprising CDR1 of SEQ ID NO: 43, CDR2 of SEQ ID NO: 44, and CDR3 of SEQ ID NO: 45.

2. The antibody of claim 1, wherein the antibody is capable of inducing homotypic adhesion of B10 cells.

3. The antibody of claim 2, wherein the antibody comprises an Fc portion of a human or humanized IgG4 antibody.

4. The antibody of claim 1, wherein the antibody comprises an Fc region which has been engineered to neither activate complement nor participate in antibody-dependent cell-mediated cytotoxicity (ADCC).

5. The antibody of claim 1, wherein the antibody comprises the VH CDRs of SEQ ID NOs: 27, 29, and 32 and the VL CDRs of SEQ ID NOs: 40, 41 and 42.

6. The antibody of claim 1, wherein the antibody comprises the VH CDRs of SEQ ID NOs: 27, 30, and 32 and the VL CDRs of SEQ ID NOs: 37, 38 and 39.

7. The antibody of claim 1, wherein the antibody comprises the VH CDRs of SEQ ID NOs: 28, 31, and 33 and the VL CDRs of SEQ ID NOs: 34, 35 and 36.

8. The antibody of claim 1, wherein the antibody comprises the VH CDRs of SEQ ID NOs: 27, 30, and 32 and the VL CDRs of SEQ ID NOs: 43, 44 and 45.

9. The antibody of claim 1, wherein the antibody comprises: (a) the VH of SEQ ID NO: 5 or sequences 95% identical to SEQ ID NO: 5 comprising the CDRs of SEQ ID NO: 28, 31 and 33 and (b) the VL of SEQ ID NO: 15 or sequences 95% identical to SEQ ID NO: 15 comprising the CDRs of SEQ ID NO: 34, 35 and 36.

10. A method for treating cancer or initiating, enhancing, or prolonging an anti-tumor response in an individual, the method comprising administering an antibody of claim 1 and at least one immune checkpoint inhibitor.

11. The method according to claim 10, wherein the antibody and the at least one immune checkpoint inhibitor are administered in a combination therapy regimen.

12. The method of claim 10, wherein the cancer is a solid, non-lymphoid tumor.

13. The method of claim 10, wherein the at least one immune checkpoint inhibitor is an inhibitor of an immune checkpoint selected from the group consisting of CTLA4 (Cytotoxic T-Lymphocyte-Associated protein 4, CD152), PD1 (also known as PD-1; Programmed Death 1 receptor), PD-L1, PD-L2, LAG-3 (Lymphocyte Activation Gene-3), OX40, A2AR (Adenosine A2A receptor), B7-H3 (CD276), B7-H4 (VTCN1), BTLA (B and T Lymphocyte Attenuator, CD272), IDO (Indoleamine 2,3-dioxygenase), KIR (Killer-cell Immunoglobulin-like Receptor), TIM 3 (T-cell Immunoglobulin domain and Mucin domain 3), VISTA (V-domain Ig suppressor of T cell activation), and IL-2R (interleukin-2 receptor).

14. The method of claim 10, wherein the antibody does not deplete the B10 cells via complement or antibody-dependent cytotoxicity.

15. The method of claim 10, wherein the antibody induces homotypic adhesion of B cells.

16. The method of claim 10, wherein the at least one checkpoint inhibitor is a PD-1 inhibitor, a CTLA-4 inhibitor, a IL-2-toxin fusion protein or combinations thereof.

17. A method of initiating, enhancing, or prolonging T cell activation in an individual in need thereof comprising administering an antibody of claim 1 preferentially depleting B10 cells and an immune checkpoint inhibitor.

18. The method according to claim 17, wherein the antibody preferentially depleting B10 cells and the at least one immune checkpoint inhibitor are administered in a combination therapy regimen.

19. A method of initiating or enhancing or prolonging effectiveness of an immune checkpoint inhibitor, or enabling toxicity or dose of an immune checkpoint inhibitor to be reduced, comprising administering to an individual a composition comprising the antibody of claim 1 that preferentially depletes B10 cells in a combination therapy regimen with a composition comprising at least one immune checkpoint inhibitor.

20. The antibody of claim 1, wherein the antibody is selected from the group consisting of antibodies comprising:
   (a) the VH of SEQ ID NO: 2 or sequences 95% identical to SEQ ID NO: 2 comprising the CDRs of SEQ ID NO: 27, 29 and 32 and the VL of SEQ ID NO: 19 or sequences 95% identical to SEQ ID NO: 19 comprising the CDRs of SEQ ID NO: 40, 41 and 42;
   (b) the VH of SEQ ID NO: 3 or sequences 95% identical to SEQ ID NO: 3 comprising the CDRs of SEQ ID NO: 27, 30 and 32 and the VL of SEQ ID NO: 16 or sequences 95% identical to SEQ ID NO: 16 comprising the CDRs of SEQ ID NO: 37, 38 and 39; and
   (c) the VH of SEQ ID NO: 4 or sequences 95% identical to SEQ ID NO: 4 comprising the CDRs of SEQ ID NO: 27, 30 and 32 and the VL of SEQ ID NO: 20 or sequences 95% identical to SEQ ID NO: 20 comprising the CDRs of SEQ ID NO: 43, 44 and 45.

* * * * *

SEQUENCE LISTING

<160> NUMBER OF SEQ ID NOS: 45

<210> SEQ ID NO 1
<211> LENGTH: 116
<212> TYPE: PRT
<213> ORGANISM: Artificial Sequence
<220> FEATURE:
<223> OTHER INFORMATION: Synthetic: LL2

<400> SEQUENCE: 1

```
Gln Val Gln Leu Gln Glu Ser Gly Ala Glu Leu Ser Lys Pro Gly Ala
1               5                   10                  15

Ser Val Lys Met Ser Cys Lys Ala Ser Gly Tyr Thr Phe Thr Ser Tyr
            20                  25                  30

Trp Leu His Trp Ile Lys Gln Arg Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115
```

<210> SEQ ID NO 2
<211> LENGTH: 117
<212> TYPE: PRT
<213> ORGANISM: Artificial Sequence
<220> FEATURE:
<223> OTHER INFORMATION: Synthetic: HB22-103

<400> SEQUENCE: 2

```
Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Arg Gly Thr Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Tyr Asp Pro Asp Tyr Trp Gly Gln Gly Thr Thr
            100                 105                 110

Leu Thr Val Ser Ser
        115
```

<210> SEQ ID NO 3
<211> LENGTH: 117
<212> TYPE: PRT
<213> ORGANISM: Artificial Sequence
<220> FEATURE:
<223> OTHER INFORMATION: Synthetic: HB22-106

<400> SEQUENCE: 3

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Met Ile His Pro Asn Ser Gly Ser Thr Asn Tyr Ser Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Tyr Asp Pro Asp Tyr Trp Gly Gln Gly Thr Thr
            100                 105                 110

Leu Thr Val Ser Ser
        115

<210> SEQ ID NO 4
<211> LENGTH: 117
<212> TYPE: PRT
<213> ORGANISM: Artificial Sequence
<220> FEATURE:
<223> OTHER INFORMATION: Synthetic: HB22-115

<400> SEQUENCE: 4

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Met Ile His Pro Asn Ser Gly Ser Thr Asn Tyr Ser Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Tyr Asp Pro Asp Tyr Trp Gly Gln Gly Thr Thr
            100                 105                 110

Leu Thr Val Ser Ser
        115

<210> SEQ ID NO 5
<211> LENGTH: 124
<212> TYPE: PRT
<213> ORGANISM: Artificial Sequence
<220> FEATURE:
<223> OTHER INFORMATION: Synthetic: HB22-107

<400> SEQUENCE: 5

Asp Val Lys Leu Val Glu Ser Gly Glu Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Tyr Ile Thr Ser Gly Gly Asp Tyr Ile Tyr Tyr Ala Asp Thr Val 50                  55                  60

Lys Gly Arg Phe Thr Ile Ser Arg Asp Asp Ala Arg Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Asp Gln Gly Tyr Tyr Tyr Asp Gly Arg Pro Thr Trp Phe Ala
             100                 105                 110

Tyr Trp Gly Gln Gly Thr Leu Val Thr Val Ser Ala
         115                 120

<210> SEQ ID NO 6
<211> LENGTH: 123
<212> TYPE: PRT
<213> ORGANISM: Artificial Sequence
<220> FEATURE:
<223> OTHER INFORMATION: Synthetic: RFB4

<400> SEQUENCE: 6

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Ala Phe Ser Ile Tyr
                 20                  25                  30

Asp Met Ser Trp Val Arg Gln Thr Pro Glu Lys Arg Leu Glu Trp Val
             35                  40                  45

Ala Tyr Ile Ser Ser Gly Gly Gly Thr Thr Tyr Tyr Pro Asp Thr Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Ser Gly Tyr Gly Ser Ser Tyr Gly Val Leu Phe Ala Tyr
             100                 105                 110

Trp Gly Gln Gly Thr Leu Val Thr Thr Ser Ala
         115                 120

<210> SEQ ID NO 7
<211> LENGTH: 121
<212> TYPE: PRT
<213> ORGANISM: Artificial Sequence
<220> FEATURE:
<223> OTHER INFORMATION: Synthetic: HB22-13

<400> SEQUENCE: 7

Glu Val Gln Leu Gln Glu Ser Gly Gly Gly Leu Val Gln Pro Gly Gly
 1               5                  10                  15

Ser Leu Arg Leu Ser Cys Ala Thr Ser Gly Phe Thr Phe Ile Asp Tyr
                 20                  25                  30

Tyr Met Asn Trp Val Arg Gln Pro Pro Gly Lys Ala Leu Glu Trp Leu
             35                  40                  45

Gly Phe Ile Lys Asn Lys Phe Asn Gly Tyr Thr Thr Glu Tyr Asn Thr
         50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Ala Glu Asp Ser Ala Thr Tyr
                 85                  90                  95

Tyr Cys Ala Arg Gly Leu Gly Arg Ser Tyr Ala Met Asp Tyr Trp Gly
             100                 105                 110

Gln Gly Thr Ser Val Thr Val Ser Ser
        115                 120

<210> SEQ ID NO 8
<211> LENGTH: 119
<212> TYPE: PRT
<213> ORGANISM: Artificial Sequence
<220> FEATURE:
<223> OTHER INFORMATION: Synthetic: HB22-23

<400> SEQUENCE: 8

Glu Val Gln Leu Gln Glu Ser Gly Gly Gly Leu Gly Ala Thr Trp Arg
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Ile
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Tyr Asp Gly Ser Ser Arg Asp Tyr Trp Gly Gln Gly
            100                 105                 110

Thr Thr Leu Thr Val Ser Ser
        115

<210> SEQ ID NO 9
<211> LENGTH: 120
<212> TYPE: PRT
<213> ORGANISM: Artificial Sequence
<220> FEATURE:
<223> OTHER INFORMATION: Synthetic: HB22-196

<400> SEQUENCE: 9

Glu Val Gln Leu Gln Glu Ser Gly Pro Asp Leu Val Lys Pro Gly Ala
1               5                   10                  15

Ser Val Lys Ile Ser Cys Lys Ala Ser Gly Tyr Ser Phe Ile Gly Tyr
            20                  25                  30

Tyr Met His Trp Leu Lys Gln Ser His Gly Lys Ser Leu Glu Trp Ile
        35                  40                  45

Gly Arg Val Asn Pro Asn Thr Ala Gly Leu Thr Tyr Asn Gln Arg Phe
    50                  55                  60

Lys Asp Lys Ala Ile Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Ser Arg Val Asp Tyr Asp Asp Tyr Gly Tyr Trp Phe Phe Asp Val Trp
            100                 105                 110

Gly Ala Gly Thr Thr Val Thr Val
        115                 120

<210> SEQ ID NO 10
<211> LENGTH: 119
<212> TYPE: PRT
<213> ORGANISM: Artificial Sequence
<220> FEATURE:
<223> OTHER INFORMATION: Synthetic: HB22-5

```
<400> SEQUENCE: 10

Glu Val Gln Leu Gln Glu Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Lys Gln Ser His Gly Lys Asn Leu Glu Trp Ile
        35                  40                  45

Gly Leu Leu His Pro Phe Asn Gly Gly Thr Ser Tyr Asn Gln Lys Phe
    50                  55                  60

Lys Gly Lys Ala Thr Leu Ser Val Asp Lys Ser Ser Thr Ala Phe
65                  70                  75                  80

Met Glu Leu Leu Ser Leu Thr Ser Glu Asp Ser Ala Val Tyr Phe Cys
                85                  90                  95

Ala Arg Gly Thr Gly Arg Asn Tyr Ala Met Asp Tyr Trp Gly Gln Gly
            100                 105                 110

Thr Ser Val Thr Val Ser Ser
        115

<210> SEQ ID NO 11
<211> LENGTH: 121
<212> TYPE: PRT
<213> ORGANISM: Artificial Sequence
<220> FEATURE:
<223> OTHER INFORMATION: Synthetic: M5/44

<400> SEQUENCE: 11

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Arg Phe Thr Asn Tyr
            20                  25                  30

Trp Ile His Trp Val Lys Gln Arg Pro Gly Gln Gly Leu Glu Trp Ile
        35                  40                  45

Gly Gly Ile Asn Pro Gly Asn Asn Tyr Thr Thr Tyr Lys Arg Asn Leu
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
        115                 120

<210> SEQ ID NO 12
<211> LENGTH: 117
<212> TYPE: PRT
<213> ORGANISM: Artificial Sequence
<220> FEATURE:
<223> OTHER INFORMATION: Synthetic: HB22-7

<400> SEQUENCE: 12

Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ser Asp Tyr
            20                  25                  30

Gly Val Asn Trp Val Arg Gln Ile Pro Gly Lys Gly Leu Glu Trp Leu
        35                  40                  45
```

Gly Ile Ile Trp Gly Asp Gly Arg Thr Asp Tyr Asn Ser Ala Leu Lys
    50                  55                  60

Ser Arg Leu Asn Ile Ser Lys Asp Asn Ser Lys Ser Gln Val Phe Leu
65                  70                  75                  80

Lys Met Asn Ser Leu Lys Ala Asp Asp Thr Ala Arg Tyr Tyr Cys Ala
                85                  90                  95

Arg Ala Pro Gly Asn Arg Ala Met Glu Tyr Trp Gly Gln Gly Thr Ser
            100                 105                 110

Val Thr Val Ser Ser
            115

<210> SEQ ID NO 13
<211> LENGTH: 117
<212> TYPE: PRT
<213> ORGANISM: Artificial Sequence
<220> FEATURE:
<223> OTHER INFORMATION: Synthetic: HB22-33

<400> SEQUENCE: 13

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Arg Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Leu
65                  70                  75                  80

Lys Leu Asn Ser Val Thr Thr Glu Asp Thr Ala Thr Tyr Tyr Cys Ala
                85                  90                  95

Arg Gly Gly Ile Thr Val Ala Met Asp Tyr Trp Gly Gln Gly Thr Ser
            100                 105                 110

Val Thr Val Ser Ser
            115

<210> SEQ ID NO 14
<211> LENGTH: 112
<212> TYPE: PRT
<213> ORGANISM: Artificial Sequence
<220> FEATURE:
<223> OTHER INFORMATION: Synthetic: LL2

<400> SEQUENCE: 14

Asp Ile Gln Leu Thr Gln Ser Pro Ser Ser Leu Ala Val Ser Ala Gly
1               5                   10                  15

Glu Asn Val Thr Met Ser Cys Lys Ser Ser Gln Ser Val Leu Tyr Ser
                20                  25                  30

Ala Asn His Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Arg Val Gln Val Glu Asp Leu Ala Ile Tyr Tyr Cys His Gln
                85                  90                  95

Tyr Leu Ser Ser Trp Thr Phe Gly Gly Gly Thr Lys Leu Glu Ile Lys
            100                 105                 110

<210> SEQ ID NO 15
<211> LENGTH: 113
<212> TYPE: PRT
<213> ORGANISM: Artificial Sequence
<220> FEATURE:
<223> OTHER INFORMATION: Synthetic: HB22-107

<400> SEQUENCE: 15

Asp Ile Val Met Ile Gln Ser Pro Ser Ser Leu Ala Met Ser Val Gly
1               5                   10                  15

Gln Lys Val Thr Met Arg Cys Lys Ser Ser Gln Ser Leu Leu Ser Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 16
<211> LENGTH: 112
<212> TYPE: PRT
<213> ORGANISM: Artificial Sequence
<220> FEATURE:
<223> OTHER INFORMATION: Synthetic: HB22-106

<400> SEQUENCE: 16

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 17
<211> LENGTH: 112
<212> TYPE: PRT
<213> ORGANISM: Artificial Sequence
<220> FEATURE:
<223> OTHER INFORMATION: Synthetic: HB22-33

<400> SEQUENCE: 17

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser

```
                    20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: Synthetic: M5/44

<400> SEQUENCE: 18

Asp Val Val Val Thr Gln Thr Pro Leu Ser Leu Pro Val Ser Phe Gly
 1               5                  10                  15

Asp Gln Val Ser Ile Ser Cys Arg Ser Ser Gln Ser Leu Ala Asn Ser
                20                  25                  30

Tyr Gly Asn Thr Phe Leu Ser Trp Tyr Leu His Lys Pro Gly Gln Ser
            35                  40                  45

Pro Gln Leu Leu Ile Tyr Gly Ile Ser Asn Arg Phe Ser Gly Val Pro
        50                  55                  60

Asp Arg Phe Thr Gly Ser Gly Ser Gly Thr Asp Phe Thr Leu Lys Ile
 65                  70                  75                  80

Ser Thr Ile Lys Pro Glu Asp Leu Gly Met Tyr Tyr Cys Leu Gln Gly
                85                  90                  95

Thr His Gln Pro Tyr Thr Phe Gly Gly Gly Thr Lys Leu Glu Ile Lys
            100                 105                 110

<210> SEQ ID NO 19
<211> LENGTH: 107
<212> TYPE: PRT
<213> ORGANISM: Artificial Sequence
<220> FEATURE:
<223> OTHER INFORMATION: Synthetic: HB22-103

<400> SEQUENCE: 19

Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Ser Asn Asn
                20                  25                  30

Leu His Trp Phe Gln Gln Lys Ser His Glu Ser Pro Arg Leu Leu Ile
            35                  40                  45

Lys Tyr Gly Tyr Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Tyr Arg Trp Pro Tyr
                85                  90                  95

Thr Phe Gly Gly Gly Thr Lys Leu Glu Ile Lys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: Synthetic: HB22-115

<400> SEQUENCE: 20

```
Asp Ile Val Leu Thr Gln Ser Pro Ala Thr Leu Ser Val Thr Pro Gly
1               5                   10                  15

Asp Ser Val Thr Leu Ser Cys Arg Ala Ser Gln Gly Ile Ser Asn Asn
            20                  25                  30

Leu His Trp Tyr Gln Gln Ser His Glu Ser Pro Arg Leu Leu Ile
        35                  40                  45

Lys Phe Thr Ser Gln Ser Val Ser Gly Ile Pro Ser Arg Phe Ser Gly
    50                  55                  60

Ser Gly Ser Gly Thr Asp Phe Thr Leu Ser Val Asn Ser Val Glu Thr
65                  70                  75                  80

Glu Asp Phe Gly Met Tyr Phe Cys Gln Gln Ser Asn Arg Trp Pro Tyr
                85                  90                  95

Thr Phe Gly Gly Gly Thr Lys Leu Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic: RFB4

<400> SEQUENCE: 21

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 22
<211> LENGTH: 107
<212> TYPE: PRT
<213> ORGANISM: Artificial Sequence
<220> FEATURE:
<223> OTHER INFORMATION: Synthetic: HB22-196

<400> SEQUENCE: 22

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
```

```
                35                  40                  45
Tyr Gly Ala Ser Asn Arg Tyr Thr Gly Val Pro Asp Arg Phe Thr Gly
             50                  55                  60
Ser Gly Ser Ala Thr Asp Phe Thr Leu Thr Ile Ser Ser Val Gln Ala
 65                  70                  75                  80
Glu Asp Leu Ala Asp Tyr His Cys Gly Gln Gly Tyr Ser Tyr Pro Tyr
                 85                  90                  95
Thr Phe Gly Gly Gly Thr Lys Leu Glu Ile Lys
                100                 105
```

```
<210> SEQ ID NO 23
<211> LENGTH: 107
<212> TYPE: PRT
<213> ORGANISM: Artificial Sequence
<220> FEATURE:
<223> OTHER INFORMATION: Synthetic: HB22-23

<400> SEQUENCE: 23

Ser Ile Val Met Thr Gln Thr Pro Lys Phe Leu Leu Val Ser Ala Gly
 1               5                  10                  15
Asp Arg Val Thr Ile Ser Cys Lys Ala Ser Gln Ser Val Ser Asn Asp
                20                  25                  30
Val Ala Trp Tyr Gln Gln Lys Pro Gly Gln Ser Pro Lys Leu Leu Ile
             35                  40                  45
Tyr Tyr Ala Ser Lys Arg Tyr Thr Gly Val Pro Asp Arg Leu Thr Gly
             50                  55                  60
Ser Gly Tyr Gly Thr Asp Phe Thr Phe Thr Ile Ser Thr Val Gln Ala
 65                  70                  75                  80
Glu Asp Leu Ala Val Tyr Phe Cys Gln Gln Asp His Ser Tyr Pro Trp
                 85                  90                  95
Thr Phe Gly Gly Gly Thr Lys Leu Glu Ile Lys
                100                 105
```

```
<210> SEQ ID NO 24
<211> LENGTH: 107
<212> TYPE: PRT
<213> ORGANISM: Artificial Sequence
<220> FEATURE:
<223> OTHER INFORMATION: Synthetic: HB22-7

<400> SEQUENCE: 24

Ser Ile Val Met Thr Gln Thr Pro Lys Phe Leu Leu Val Ser Ala Gly
 1               5                  10                  15
Asp Arg Ile Thr Leu Thr Cys Lys Ala Ser Gln Ser Val Thr Asn Asp
                20                  25                  30
Val Ala Trp Tyr Gln Gln Lys Pro Gly Gln Ser Pro Lys Leu Leu Ile
             35                  40                  45
Tyr Tyr Ala Ser Asn Arg Tyr Thr Gly Val Pro Asp Arg Phe Thr Gly
             50                  55                  60
Ser Gly Tyr Gly Thr Asp Phe Thr Phe Thr Ile Ser Thr Val Gln Ala
 65                  70                  75                  80
Glu Asp Leu Ala Val Tyr Phe Cys Gln Gln Asp Tyr Arg Ser Pro Trp
                 85                  90                  95
Thr Phe Gly Gly Gly Thr Lys Leu Glu Ile Lys
                100                 105
```

```
<210> SEQ ID NO 25
<211> LENGTH: 107
```

```
<212> TYPE: PRT
<213> ORGANISM: Artificial Sequence
<220> FEATURE:
<223> OTHER INFORMATION: Synthetic: HB22-5

<400> SEQUENCE: 25

Ser Ile Val Met Thr Gln Thr Pro Lys Phe Leu Leu Val Ser Thr Gly
1               5                   10                  15

Asp Arg Val Thr Ile Thr Cys Lys Ala Ser Gln Thr Val Thr Asn Asp
            20                  25                  30

Leu Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Asn Thr Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Leu Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: Synthetic: HB22-13

<400> SEQUENCE: 26

Ser Ile Val Met Thr Gln Thr Pro Lys Phe Leu Leu Val Ser Ala Gly
1               5                   10                  15

Asp Arg Val Ser Ile Thr Cys Lys Ala Ser Gln Ser Val Thr Asn Asp
            20                  25                  30

Val Thr Trp Tyr Gln Gln Lys Pro Gly Gln Ser Pro Lys Leu Leu Ile
        35                  40                  45

Tyr Phe Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Leu Lys
            100                 105

<210> SEQ ID NO 27
<211> LENGTH: 8
<212> TYPE: PRT
<213> ORGANISM: Artificial Sequence
<220> FEATURE:
<223> OTHER INFORMATION: Synthetic: HB22-103 HB22-106, HB22-115 VH CDR1

<400> SEQUENCE: 27

Gly Tyr Thr Phe Thr Ser Tyr Trp
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic: HB22-107 VH CDR1
```

```
<400> SEQUENCE: 28

Gly Phe Thr Phe Ser Ser Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic: HB22-103 VH CDR2

<400> SEQUENCE: 29

Ile His Pro Asn Arg Gly Thr Thr
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic: HB22-106 and HB22-115 VH CDR2

<400> SEQUENCE: 30

Ile His Pro Asn Ser Gly Ser Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic: HB22-107 VH CDR2

<400> SEQUENCE: 31

Ile Thr Ser Gly Gly Asp Tyr Ile
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic: HB22-103, HB22-106 and HB22-115 VH
      CDR3

<400> SEQUENCE: 32

Ala Arg Tyr Tyr Asp Tyr Asp Pro Asp Tyr
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Synthetic: HB22-107 VH CDR3

<400> SEQUENCE: 33

Thr Arg Asp Gln Gly Tyr Tyr Tyr Asp Gly Arg Pro Thr Trp Phe Ala
1               5                   10                  15

Tyr

<210> SEQ ID NO 34
<211> LENGTH: 12
<212> TYPE: PRT
<213> ORGANISM: Artificial Sequence
```

```
<220> FEATURE:
<223> OTHER INFORMATION: Synthetic: HB22-107 VL CDR1

<400> SEQUENCE: 34

Gln Ser Leu Leu Ser Ser Asn Gln Lys Asn Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Synthetic: HB22-107 VL CDR2

<400> SEQUENCE: 35

Phe Ala Ser
1

<210> SEQ ID NO 36
<211> LENGTH: 9
<212> TYPE: PRT
<213> ORGANISM: Artificial Sequence
<220> FEATURE:
<223> OTHER INFORMATION: Synthetic: HB22-107 VL CDR3

<400> SEQUENCE: 36

Gln Gln His Tyr Ser Thr Pro Leu Thr
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic: HB22-106 VL CDR1

<400> SEQUENCE: 37

Gln Ser Leu Leu Asp Ser Asp Gly Lys Thr Tyr
1               5                   10

<210> SEQ ID NO 38
<211> LENGTH: 3
<212> TYPE: PRT
<213> ORGANISM: Artificial Sequence
<220> FEATURE:
<223> OTHER INFORMATION: Synthetic: HB22-106 VL CDR2

<400> SEQUENCE: 38

Leu Val Ser
1

<210> SEQ ID NO 39
<211> LENGTH: 9
<212> TYPE: PRT
<213> ORGANISM: Artificial Sequence
<220> FEATURE:
<223> OTHER INFORMATION: Synthetic: HB22-106 VL CDR3

<400> SEQUENCE: 39

Trp Gln Gly Thr His Phe Pro Arg Thr
1               5

<210> SEQ ID NO 40
<211> LENGTH: 6
<212> TYPE: PRT
<213> ORGANISM: Artificial Sequence
<220> FEATURE:
```

<223> OTHER INFORMATION: Synthetic: HB22-103 VL CDR1

<400> SEQUENCE: 40

Gln Ser Ile Ser Asn Asn
1               5

<210> SEQ ID NO 41
<211> LENGTH: 3
<212> TYPE: PRT
<213> ORGANISM: Artificial Sequence
<220> FEATURE:
<223> OTHER INFORMATION: Synthetic: HB22-103 VL CDR2

<400> SEQUENCE: 41

Tyr Gly Tyr
1

<210> SEQ ID NO 42
<211> LENGTH: 9
<212> TYPE: PRT
<213> ORGANISM: Artificial Sequence
<220> FEATURE:
<223> OTHER INFORMATION: Synthetic: HB22-103 VL CDR3

<400> SEQUENCE: 42

Gln Gln Ser Tyr Arg Trp Pro Tyr Thr
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic: HB22-115 VL CDR1

<400> SEQUENCE: 43

Gln Gly Ile Ser Asn Asn
1               5

<210> SEQ ID NO 44
<211> LENGTH: 3
<212> TYPE: PRT
<213> ORGANISM: Artificial Sequence
<220> FEATURE:
<223> OTHER INFORMATION: Synthetic: HB22-115 VL CDR2

<400> SEQUENCE: 44

Phe Thr Ser
1

<210> SEQ ID NO 45
<211> LENGTH: 9
<212> TYPE: PRT
<213> ORGANISM: Artificial Sequence
<220> FEATURE:
<223> OTHER INFORMATION: Synthetic: HB22-115 VL CDR3

<400> SEQUENCE: 45

Gln Gln Ser Asn Arg Trp Pro Tyr Thr
1               5